(12) United States Patent
Brestel et al.

(10) Patent No.: US 10,949,968 B2
(45) Date of Patent: Mar. 16, 2021

(54) SYSTEMS AND METHODS FOR DETECTING AN INDICATION OF A VISUAL FINDING TYPE IN AN ANATOMICAL IMAGE

(71) Applicant: Zebra Medical Vision Ltd., Shefayim (IL)

(72) Inventors: Chen Brestel, Rehovot (IL); Eli Goz, Herzlia (IL); Jonathan Laserson, Tel Aviv (IL)

(73) Assignee: Zebra Medical Vision Ltd., Shefeyim (IL)

( * ) Notice: Subject to any disclaimer, the term of this patent is extended or adjusted under 35 U.S.C. 154(b) by 110 days.

(21) Appl. No.: 16/269,633

(22) Filed: Feb. 7, 2019

(65) Prior Publication Data

US 2019/0340753 A1     Nov. 7, 2019

Related U.S. Application Data

(63) Continuation-in-part of application No. 15/972,912, filed on May 7, 2018, now Pat. No. 10,706,545.

(51) Int. Cl.
*G06N 3/08* (2006.01)
*G06T 7/00* (2017.01)
(Continued)

(52) U.S. Cl.
CPC .......... *G06T 7/0012* (2013.01); *G06N 3/084* (2013.01); *G16H 15/00* (2018.01); *G16H 50/20* (2018.01);
(Continued)

(58) Field of Classification Search
None
See application file for complete search history.

(56) References Cited

U.S. PATENT DOCUMENTS

| 5,857,030 A | 1/1999 | Gaborski et al. |
| 10,631,812 B2 | 4/2020 | Westerhoff et al. |

(Continued)

FOREIGN PATENT DOCUMENTS

| WO | WO 2018/015414 | 1/2018 |
| WO | WO 2019/215604 | 11/2019 |

(Continued)

OTHER PUBLICATIONS

International Search Report and the Written Opinion dated Sep. 25, 2019 From the International Searching Authority Re. Application No. PCT/IB2019/053726. (11 Pages).

(Continued)

*Primary Examiner* — Idowu O Osifade

(57) ABSTRACT

There is provided a system for computing a single-label neural network for detection of an indication of an acute medical condition, comprising: hardware processor(s) executing a code for: providing a multi-label training dataset including anatomical images each associated with a label indicative of visual finding type(s), or indicative of no visual finding types, training a multi-label neural network for detection of the visual finding types(s) in a target anatomical image according to the multi-label training dataset, creating a single-label training dataset including anatomical images each associated with a label indicative of the selected single visual finding type, or indicative of an absence of the single visual finding type, and training a single-label neural network for detection of the single visual finding type, by setting the trained multi-label neural network as an initial baseline of the single-label neural network, and fine-tuning and/or re-training the baseline according to the single-label training dataset.

22 Claims, 6 Drawing Sheets

(51) Int. Cl.

| | |
|---|---|
| *G16H 15/00* | (2018.01) |
| *G16H 50/20* | (2018.01) |
| *A61B 6/03* | (2006.01) |
| *G16H 50/50* | (2018.01) |
| *G16H 40/63* | (2018.01) |
| *A61B 5/055* | (2006.01) |

(52) U.S. Cl.
CPC .............. *A61B 5/055* (2013.01); *A61B 6/032* (2013.01); *G06T 2207/10081* (2013.01); *G06T 2207/10088* (2013.01); *G06T 2207/30004* (2013.01); *G16H 40/63* (2018.01); *G16H 50/50* (2018.01)

(56) References Cited

U.S. PATENT DOCUMENTS

| | | |
|---|---|---|
| 2006/0110021 A1 | 5/2006 | Luo et al. |
| 2010/0161022 A1 | 6/2010 | Tolkowsky |
| 2010/0284590 A1 | 11/2010 | Peng et al. |
| 2011/0188706 A1 | 8/2011 | Zhou |
| 2011/0257919 A1 | 10/2011 | Reiner |
| 2012/0172700 A1 | 7/2012 | Krishnan et al. |
| 2013/0129165 A1 | 5/2013 | Dekel et al. |
| 2015/0049163 A1 | 2/2015 | Smurro |
| 2015/0261915 A1 | 9/2015 | Yanagida et al. |
| 2015/0262014 A1 | 9/2015 | Iwamura et al. |
| 2015/0279061 A1 | 10/2015 | Kutsuna et al. |
| 2017/0046483 A1 | 2/2017 | Reicher et al. |
| 2017/0221204 A1 | 8/2017 | Shinagawa |
| 2018/0101645 A1 | 4/2018 | Sorenson et al. |
| 2018/0259608 A1 | 9/2018 | Golden et al. |
| 2019/0110753 A1* | 4/2019 | Zhang .................... G06N 3/084 |
| 2019/0156484 A1 | 5/2019 | Nye et al. |
| 2019/0209022 A1* | 7/2019 | Sobol .................... A61B 5/1112 |
| 2019/0340752 A1 | 11/2019 | Brestel et al. |
| 2019/0340763 A1 | 11/2019 | Laserson |
| 2019/0350657 A1 | 11/2019 | Tolkowsky |

FOREIGN PATENT DOCUMENTS

| | | |
|---|---|---|
| WO | WO 2019/215605 | 11/2019 |
| WO | WO 2019/215606 | 11/2019 |

OTHER PUBLICATIONS

Brady et al. "Discrepancy and Error in Radiology: Concepts, Causes and Consequences", The Ulster Medical Journal, 81(1): 3-9, Jan. 2012.

Bruno et al. "Understanding and Confronting Our Mistakes: The Epidemiology of Error in Radiology and Strategies for Error Reduction", RadioGraphics, 35(6): 1668-1676, Published Online Oct. 14, 2015.

Demner-Fushman et al. "Annotation of Chest Radiology Reports for Indexing and Retrieval", Proceedings of the First International Workshop on Multimodal Retrieval in the Medical Domain, MRDM '15, Vienna, Austria, Mar. 29, 2015, LNCS 9059: 99-111, Mar. 29, 2015.

Hanna et al. "Effect of Shift, Schedule, and Volume on Interpretice Accuracy: A Retrospective Analysis of 2.9 Million Radiologic Examinations", Radiology, 287(1): 205-212, Published Online Nov. 20, 2017.

Huang et al. "Densely Connected Convolutional Networks", Proceedings of the IEEE Conference on Computer Vision and Pattern Recognition, CVPR '17, Honolulu, Hawaii, USA, Jul. 21-26, 2017, p. 4700-4708, Jul. 21, 2017.

Jing et al. "On the Automatic Generation of Medical Imaging Reports", arXiv:1711.08195v1, p. 1-9, Nov. 22, 2017.

Rajpurkar et al. "CheXNet: Radiologist-Level Pneumonia Detection on Chest X-Rays With Deep Learning", arXiv:1711.05225v1, 7 P., Nov. 14, 2017.

Robinson et al. "Variation Between Experienced Observers in the Interpretation of Accident and Emergency Radiographs", The British Journal of Radiology, 72: (856): 323-330, Apr. 1999.

Shin et al. "Learning to Read Chest X-Rays: Recurrent Neural Cascade Model for Automated Image Annotation", Proceedings of the IEEE Conference of Computer Vision and Pattern Recognition, CVPR '16, Las Vegas, NV, USA, Jun. 27-30, 2016, p. 2497-2506, Jun. 27, 2016.

Taylor et al. "Automated Detection of Moderate and Large Pneumothorax on Frontal Chest X-rays Using Deep Convolutional Neural Networks: A Retrospective Study", PLoS Medicine, 15(11): e1002697, pp. 1-15, Nov. 20, 2018.

Wang et al. "ChestX-Ray8: Hospital-Scale Chest X-Ray Database and Benchmarks on Weakly-Supervised Classification and Localization of Common Thorax Diseases", Proceedings of the IEEE Conference on Computer Vision and Pattern Recognition, CVPR '17, Honolulu, Hawaii, USA, Jul. 21-26, 2017, p. 2097-2106, Jul. 21, 2017.

International Search Report and the Written Opinion dated Sep. 8, 2019 From the International Searching Authority Re. Application No. PCT/IB2019/053725. (9 Pages).

International Search Report and the Written Opinion dated Sep. 12, 2019 From the International Searching Authority Re. Application No. PCT/IB2019/053724. (12 Pages).

Dong et al. "Learning to Read Chest X-Ray Images From 16000+ Examples Using CNN", 2017 Proceedings of the IEEE/ACM International Conference on Connected Health: Applications, Systems and Engineering Technologies, CHASE, Philadelphia, PA, USA, Jul. 17-19, 2017, p. 51-57, Jul. 17, 2017.

Kamnitsas et al. "Efficient Multi-Scale 3D CNN With Fully Connected CRF for Accurate Brain Lesion Segmentation", Medical Image Analysis, 36: 61-78, Available Online Oct. 29, 2016.

Mayer et al. "Transfer Learning for Data Triage Applications", IS&T International Symposium on Electronic Imaging 2018, Visual Information Processing and Communication IX, p. 175-1-175-6, Jan. 1, 2018.

Official Action dated Dec. 13, 2019 From the US Patent and Trademark Office Re. U.S. Appl. No. 15/972,912. (37 pages).

European Search Report and the European Search Opinion dated Sep. 26, 2019 From the European Patent Office Re. Application No. 19173136.3. (8 Pages).

De Vos et al. "ConvNet-Based Localization of Anatomical Structures in 3D Medical Images", ARXIV.Org, Cornell University Library, XP080763925, ArXiv:1704.05629v1, p. 1-12, Apr. 19, 2017.

International Preliminary Report on Patentability dated Nov. 19, 2020 From the International Bureau of WIPO Re. Application No. PCT/IB2019/053724. (8 Pages).

Official Action dated Aug. 21, 2020 from the US Patent and Trademark Office Re. U.S. Appl. No. 16/269,619. (113 pages).

DICOM "About DICOM: Overview", Retrieved from the Internet on Sep. 1, 2020, 1 page.

International Preliminary Report on Patentability dated Nov. 19, 2020 From the International Bureau of WIPO Re. Application No. PCT/IB2019/053725. (6 Pages).

\* cited by examiner

| Model | Color | AUC | MiniAUC Target FPR 85%, Tolerance +-2 | Comment |
|---|---|---|---|---|
| ens_010_3_mdls | Green | 95.1% | 93.8% | (1) Better for the product target by 0.2% according to MiniAUC (2) Actual Sp is better by 0.9% at the product target! (3) AUC predicts vise versa, that it has a smaller AUC by 0.2% |
| ens_011_4_mdls | Blue | 95.3% | 93.6% | |

FIG. 5

SYSTEMS AND METHODS FOR DETECTING AN INDICATION OF A VISUAL FINDING TYPE IN AN ANATOMICAL IMAGE

RELATED APPLICATIONS

This application is a Continuation-In-Part (CIP) of U.S. patent application Ser. No. 15/972,912 filed on May 7, 2018.

This application is also related to co-filed U.S. Continuation-In-Part (CIP) patent application Ser. No. 16/696,619 titled "SYSTEMS AND METHODS FOR PRE-PROCESSING ANATOMICAL IMAGES FOR FEEDING INTO A CLASSIFICATION NEURAL NETWORK".

The contents of the above applications are all incorporated by reference as if fully set forth herein in their entirety.

FIELD AND BACKGROUND OF THE INVENTION

The present invention, in some embodiments thereof, relates to medical anatomical images and, more specifically, but not exclusively, to systems and methods for automated analysis of medical anatomical images.

Manual visual assessment (e.g., by a radiologist) of medical anatomical images, such as x-ray images, is a challenging and time consuming task due to the large amount of information that needs to be processed. The radiologist looks to identify relevant features of the anatomical images when a large number of possible features are possible. For example, each medical anatomical image includes multiple anatomical objects, such as bones, different organs, and different connective tissues, each of which may present with different findings. Critical findings, which require urgent treatment, may be missed by the radiologist.

SUMMARY OF THE INVENTION

According to a first aspect, a system for computing a single-label neural network for detection of an indication of a single visual finding type in an anatomical image of a target individual, the single visual finding type denoting an acute medical condition for early and rapid treatment thereof, comprises: at least one hardware processor executing a code for: providing a multi-label training dataset including a plurality of anatomical images each associated with a label indicative of at least one visual finding type selected from a plurality of visual findings type, or indicative of no visual finding types, training a multi-label neural network for detection of the plurality of visual finding types in a target anatomical image according to the multi-label training dataset, creating a single-label training dataset including a plurality of anatomical images each associated with a label indicative of the single visual finding type selected from the plurality of visual finding types, or indicative of an absence of the single visual finding type, and training a single-label neural network for detection of the single visual finding type in a target anatomical image, by setting the trained multi-label neural network as an initial baseline of the single-label neural network, and at least one of fine-tuning and re-training the baseline according to the single-label training dataset.

According to a second aspect, a system for detection of an indication of a single visual finding type in a target anatomical image of a target individual by a single-label neural network, the single visual finding type denoting an acute medical condition for early and rapid treatment thereof, comprises: at least one hardware processor executing a code for: feeding a target anatomical image into a single-label neural network, and computing likelihood of an indication of the single visual finding type in the target anatomical image by the single-label neural network, wherein the single-label neural network is computed by at least one of fine-tuning and retraining a trained multi-label neural networking according to a single-label training dataset of a plurality of anatomical images labeled with an indication of the visual finding type, wherein the multi-label neural network is trained to compute likelihood of each of a plurality of visual finding types based on a multi-label training dataset of a plurality of anatomical images labeled with the plurality of visual finding types.

According to a third aspect, a method of computing a single-label neural network for detection of an indication of a single visual finding type in an anatomical image of a target individual, the single visual finding type denoting an acute medical condition for early and rapid treatment thereof, comprises: providing a multi-label training dataset including a plurality of anatomical images each associated with a label indicative of at least one visual finding type selected from a plurality of visual finding types, or indicative of no visual finding types, training a multi-label neural network for detection of the plurality of visual finding types in a target anatomical image according to the multi-label training dataset, creating a single-label training dataset including a plurality of anatomical images each associated with a label indicative of the single visual finding type selected from the plurality of visual finding types, or indicative of an absence of the single visual finding type, and training a single-label neural network for detection of the single visual finding type in a target anatomical image, by setting the trained multi-label neural network as an initial baseline of the single-label neural network, and at least one of fine-tuning and re-training the baseline according to the single-label training dataset.

In a further implementation form of the first, second, and third aspects, the accuracy of the trained single-label neural network for detection of the single visual finding type in the target anatomical image is higher than the accuracy of the multi-label neural network for detection of the single visual finding type in a target anatomical image, and higher than another single-label neural network trained only on the single-label training dataset using a standard un-trained neural network as the initial baseline, and higher than another single-label neural network trained on a multi-object neural network trained to detect non-medical objects in non-medical images.

In a further implementation form of the first, second, and third aspects, detection of the single visual finding type comprises computing, by the single-label neural network, a likelihood score indicative of a probability of the single visual finding type being depicted in the target anatomical image.

In a further implementation form of the first, second, and third aspects, the anatomical image and the single visual finding type are selected from the group consisting of: two dimensional (2D) AP and/or PA and/or lateral chest x-ray and pneumothorax including a small pneumothorax, 2D AP and/or PA chest x-ray and pneumomediastinum, and 2D abdominal x-ray and pneumoperitoneum.

In a further implementation form of the first, second, and third aspects, labels of the plurality of anatomical images of the multi-label training dataset are created based on an analysis that maps individual sentences of a plurality of sentences of a respective text based radiology report to a corresponding visual finding type of the plurality of visual finding types.

In a further implementation form of the first, second, and third aspects, the multi-label neural network is trained to identify about 20-50 different visual finding types.

In a further implementation form of the first, second, and third aspects, the plurality of visual finding types include members selected from the group consisting of: abnormal aorta, aortic calcification, artificial valve, atelectasis, bronchial wall thickening, cardiac pacer, cardiomegaly, central line, consolidation, costrophrenic angle blunting, degenerative changes, elevated diaphragm, fracture, granuloma, hernia diaphragm, hilar prominence, hyperinflation, interstitial markings, kyphosis, mass, mediastinal widening, much bowel gas, nodule, orthopedic surgery, osteopenia, pleural effusion, pleural thickening, pneumothorax, pulmonary edema, rib fracture, scoliosis, soft tissue calcification, sternotomy wires, surgical clip noted, thickening of fissure, trachea deviation, transplant, tube, and vertebral height loss.

In a further implementation form of the first, second, and third aspects, training the single-label neural network comprises training a plurality of instances of the single-label neural network, wherein each instance has different neural network parameters, and further comprising: evaluating performance of each instance of the plurality of instances for detection of the indication of the single visual finding type, and creating an ensemble by selecting a combination of the instances according to a requirement of the evaluated performance, wherein single-label neural network comprises the ensemble.

In a further implementation form of the first, second, and third aspects, the different neural network parameters of the plurality of instances of the single-label neural network are selected from the group consisting of: preprocessing image size, preprocessing input size, neural network architecture modification, at least one additional intermediate dense layer before a final output, preprocessing normalization type, and standard deviation normalization.

In a further implementation form of the first, second, and third aspects, training the multi-label neural network comprises training a plurality of instances of the multi-label neural network, and selecting one of the instances having a lowest validation loss for the single visual finding, wherein training the single-label neural network comprises training the selected one instance using a checkpoint of network weights of the selected one instance.

In a further implementation form of the first, second, and third aspects, training the single-label neural network comprises training a plurality of instances of the single-label neural network varying according to at least one network parameter, and further comprising: obtaining at least one of a target sensitivity and a target specificity, and a tolerance, computing a mini-AUC (area under curve) for a region under the receiver operating characteristic (ROC) curve computed for each instance of the plurality of instances of the single-label neural network, corresponding to the at least one of the target sensitivity and target specificity within the tolerance, and selecting at least one instance of the plurality of instances of the single-label neural network according to a requirement of the mini-AUC, for inclusion in an ensemble of the single-label neural network.

In a further implementation form of the first, second, and third aspects, weights of the baseline are set according to corresponding weights of non-last fully connected layers of the trained multi-label neural network.

In a further implementation form of the first, second, and third aspects, a prevalence of the anatomical images labeled with the single visual finding type of the single-label training dataset is statistically significantly higher than a prevalence of the anatomical images labeled with the single visual finding type of the multi-label training dataset and denoting a wild prevalence of the single visual finding type in practice.

In a further implementation form of the first, second, and third aspects, the plurality of anatomical images of the multi-label training dataset are clustered into three clusters, comprising: a single visual finding type cluster including anatomical images depicting at least the single visual finding type, a general positive finding cluster including anatomical images depicting at least one of the plurality of visual finding types excluding the single visual finding type, and a negative finding cluster including anatomical images depicting none of the plurality of visual finding types, wherein the single-label training dataset is created by randomly sampling one image from each of the clusters in succession.

In a further implementation form of the first, second, and third aspects, the system further comprises code for and/or the method further comprises at least one of: diagnosing the acute medical condition and treating the patient for the acute medical condition.

In a further implementation form of the second aspect, the feeding, and the computing are iterated for each of a plurality of target anatomical images, and further comprising: generating instructions for creating a triage list for manual review by a human user of respective target anatomical images computed as likely including the indication of the visual finding type.

In a further implementation form of the first, second, and third aspects, the visual finding type denotes an acute medical condition requiring urgent treatment, wherein a time delay in diagnosis and treatment of the acute medical condition leads to increased risk of morbidity for the patient.

In a further implementation form of the first, second, and third aspects, the computed likelihood denotes a confidence score indicative of probability of the presence of the visual finding type in the anatomical image, wherein the instructions are for creating the triage list according to priority for review by the human reviewer, ranked by decreasing likelihood of the indication of the visual finding type based on the confidence score.

In a further implementation form of the first, second, and third aspects, the system further comprises code for and/or the method further comprises receiving a plurality of target anatomical images from a medical imaging storage server, feeding each one of the plurality of target anatomical images into a visual filter neural network for outputting a classification category indicative of a target body region depicted at a target sensor orientation and a rotation relative to a baseline defined by a single-label neural network, or another classification category indicative of at least one of a non-target body region and a non-target sensor orientation, rejecting a sub-set of the plurality of target anatomical images classified into the another classification category, to obtain a remaining sub-set of the plurality of target anatomical images, rotating to the baseline the remaining sub-set of the plurality of target anatomical images classified as rotated relative to the baseline, and feeding each one of the remaining sub-set of the plurality of target anatomical images into the single-label neural network for computing likelihood of an indication of the single visual finding type in the respective target anatomical image by the single-label neural network.

In a further implementation form of the first, second, and third aspects, the system further comprises code for and/or the method further comprises identifying pixels for the target anatomical image having outlier pixel intensity values denoting an injection of content, and adjusting the outlier pixel intensity values of the identified pixels to values computed as a function of non-outlier pixel intensity values, prior to the feeding the target anatomical image into the single-label neural network.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
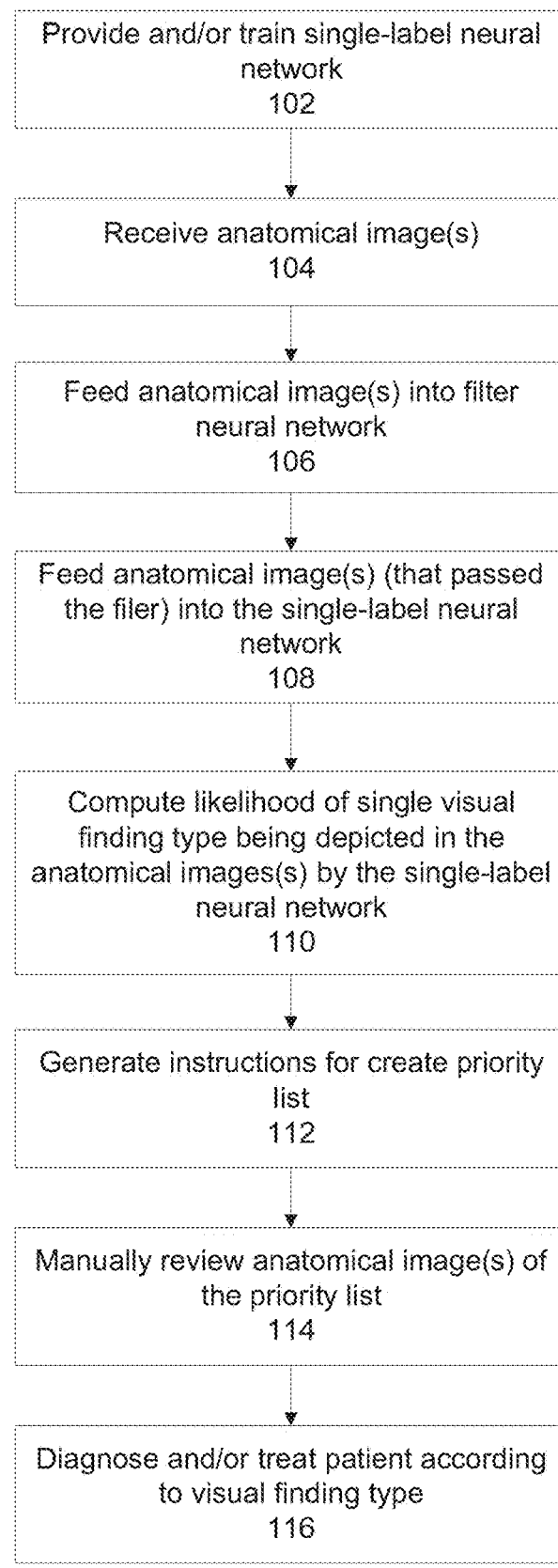
FIG. 1 is a flowchart of a method for detection of an indication of a single visual finding type in a target anatomical image of a target individual by a single-label neural network trained from a baseline of a multi-label neural network that include multiple visual finding types including the selected single visual finding type, in accordance with some embodiments of the present invention.

The present invention, in some embodiments thereof, relates to medical anatomical images and, more specifically, but not exclusively, to systems and methods for automated analysis of medical anatomical images.

An aspect of some embodiments of the present invention relates to systems, methods, an apparatus, and/or code instructions (i.e., stored on a data storage device and executable by one or more hardware processor(s)) for computing a single-label training neural network for detection of an indication of a single visual finding in an anatomical image of a target individual. The single visual finding denotes an acute medical condition for early and rapid treatment thereof, for example, pneumothorax, pneumoperitoneum, pneumomediastinum, and fracture. The single-label neural network is trained in two steps. First, a multi-label neural network is trained for detection of multiple visual finding types in a target anatomical image. The multi-label neural network is trained according to a multi-label training dataset that includes multiple anatomical images each associated with a label indicative of one or more visual finding types, or indicative of no visual findings type. Then, the single-label neural network is trained for detection of a selected single visual finding type in a target anatomical image. The single visual finding type is selected from the multiple visual finding types. The single-label neural network is trained according to a single-label training dataset storing multiple anatomical images each associated with a label indicative of the single visual finding type, or indicative of an absence of the single visual finding type. The single-label neural network is trained by setting the trained multi-label neural network as an initial baseline of the single-label neural network, and fine-tuning and/or re-training the baseline according to the single-label training dataset. For example, setting the values of the weights of the single-label neural network according to the weights of the trained multi-label neural network, and adjusting the values of the weights according to the single-label training dataset.

Optionally, an ensemble of single-label networks are trained from the baseline multi-label neural network. A target sensitivity and/or target specificity are obtained, for example, manually entered by a user. The target sensitivity and/or target specificity may be selected, for example, based on clinical requirement for detecting the selected visual finding type. For example, a certain visual finding may be indicative of a detrimental medical condition if missed by the radiologist. The sensitivity may be set to be high in such a case. In another example, correct diagnosis of the visual finding may be necessary to prevent unnecessary treatment due to an incorrect diagnosis. In such a case, the specificity may be set to be high. A mini-AUC (area under curve) may be computed for a region under the receiver operating characteristic (ROC) curve of each member of the ensemble corresponding to the target sensitivity and/or target specificity. The member(s) of the ensemble are selected according to a requirement of the mini-AUC.

As used herein, the term single-label neural network may refer to the ensemble of instances of the single-label neural network.

An aspect of some embodiments of the present invention relates to systems, methods, an apparatus, and/or code instructions (i.e., stored on a data storage device and executable by one or more hardware processor(s)) for detecting an indication of a single visual finding type in a target anatomical image of a target individual. The single visual finding type denotes an acute medical condition for early and rapid treatment thereof, for example, pneumothorax, pneumomediastinum, pneumoperitoneum, and fracture. The target anatomical image is fed into a single-label neural network that computes likelihood of the single visual finding being present in the target anatomical image. The single-label neural network is computed by fine-tuning and/or retraining a trained multi-label neural networking according to a single-label training dataset of anatomical images labeled with an indication of the selected visual finding type. The multi-label neural network is trained to compute likelihood of each of multiple visual finding types based on a multi-label training dataset of anatomical images labeled with respective visual findings.

Optionally, multiple anatomical images are analyzed by being fed into the single-label neural network. The multiple anatomical images may be stored in a centralized anatomical imaging storage server, for example, a picture archiving and communication system (PACS) server, optionally according to a medical data storage format, for example, DICOM®. A triage list of the analyzed anatomical images is created, for manual review by a user, for example, a radiologist. The triage list includes anatomical images for which a likelihood of depicting the selected visual finding type is computed, optionally ranked according to a computed probability.

As described here in additional detail, for example, in the "Examples" section below, Inventors discovered that the process of training the single-label neural network for detection of the single visual finding type, by re-training and/or fine-turning the trained multi-label neural network, provides relatively higher accuracy (e.g., sensitivity and/or specificity and/or precision) over other neural network architectures trained to detect the single visual finding type in an anatomical image. In particular, for detecting fine visual findings which may be easily missed by radiologists, and/or difficult to identify by radiologists. For example, over a standard un-trained neural network that is trained on a single-label training dataset for detecting the single visual finding type. In another example, over a standard multi object neural network that detects a plurality of different objects, none of which include visual findings of anatomical images (e.g., ImageNet), that is fine tuned and/or re-trained to detect the single visual finding type. In yet another example, over the multi-label neural network alone (created and/or trained as described herein) in terms of detecting the single visual finding type.

It is noted that detecting the visual finding type in the medical image is a more challenging task in comparison to classifying non-medical objects appearing in non-medical images (e.g., house, dog, name of person depicted in image). The visual finding type occupies a relatively small region of the anatomical image, and is generally a fine feature, making it a challenge for neural networks to extract sufficient data for accurate classification of the fine feature. In contrast, non-medical objects in non-medical images may occupy a relatively large region of the non-medical image, and since the entire object is classified rather than a finding in the object, the neural network may rely on a much larger number of features extracted from the image in order to classify the non-medical object.

It is noted that the multi-label neural network described herein is different than standard neural networks trained to detect multiple different objects in image (e.g., ImageNet) for multiple reasons: (i) the multi-label neural network described herein is designed to process anatomical images such as x-ray images, which may have a bit depth larger than the displayed depth (e.g., 10-14 vs 8), in contrast to standard neural networks that are designed to process environmental images based on visible light and not anatomical images. (ii) the multi-label neural network described herein is designed to identify multiple different visual finding types in the same context (e.g., AP chest x-ray), in contrast to standard neural networks that identify different objects in different contexts. (iii) the multi-label neural network described herein is designed to identify multiple different visual finding types, each of which may appear at different anatomical locations (e.g., different parts of the lung), may appear differently (e.g., depending on size, process of evolution), in contrast to standard neural network that identify objects that are similar to one another. (iv) the multi-label neural network described herein is designed to identify multiple different visual finding types which may be fine features that are difficult to visually detect,), in contrast to standard neural network that identify objects that are specific, well demarcated, and easy to visually detect.

At least some of the systems, methods, apparatus, and/or code instructions described herein address the medical problem of quickly identifying the presence of a visual finding in a medical image indicative of a medical problem. The visual finding may be an acute finding, which is not normally present, and representing a medical problem. The acute finding may progress or remain stable, but in either case it may be indicative of a situation that in which the clinical state of the patient is worsening. The acute finding may be indicative of the need for urgent medical treatment. Delay in treatment of the acute finding leads to increases in complications for the patient. The visual finding may be a fine feature, which may be easily missed by a radiologist. Examples of such acute, fine, easily missed visual findings include: pneumothorax in a chest x-ray, pneumomediastinum in a chest x-ray, pneumoperitoneum in an abdominal x-ray, fracture in a limb x-ray, and detection of acute appendicitis in an US of the appendix.

At least some of the systems, methods, apparatus, and/or code instructions described herein improve the technical field of automated analysis of anatomical images to identify likelihood of the presence of a visual finding in a medial image, optionally a fine visual finding, optionally representing an acute medical condition requiring urgent diagnosis and treatment, which may easily be missed by a radiologist. To identify such visual findings in anatomical images requires a classifier with high accuracy, which is not provided by any standard classifier. Such standard classifiers use an off the shelf classifier (e.g., neural network), and a training dataset of labeled anatomical images. Such standard classifiers are trained to detect a single visual finding. The improvement provided by at least some of the systems, methods, apparatus, and/or code instructions described herein includes an increase in accuracy of the automated detection process, for example, in comparison to accuracy achieved by standard automated detection processes. The increase in accuracy is obtained at least by the process of training a multi-label neural network using a multi-label training dataset to detect multiple different visual finding types in a target anatomical image, and then training a single-label neural network to detect a single visual finding type (i.e., selected from the multiple visual finding types which the multi-label neural network is trained to detect), by setting the trained multi-label neural network as a baseline neural network, optionally with one or more adjustments of neural network parameters, and fine tuning and/or re-training the baseline neural network using a single-label training dataset.

The improvement provided by at least some of the systems, methods, apparatus, and/or code instructions described herein may include a reduction in the amount of time for alerting a user (e.g., treating physician) to the presence of a visual finding type in an anatomical image for rapid diagnosis and/or treatment thereof.

At least some of the systems, methods, apparatus, and/or code instructions described herein improve the medical process of diagnosis and/or treatment of acute medical conditions in a patient, for example, within an emergency room setting. At least some of the systems, methods, apparatus, and/or code instructions described herein provide a triage system that identifies likelihood of anatomical images (e.g., chest x-rays) including a visual finding indicating an acute medical condition requiring urgent treatment, for example, pneumothorax. The medical images having identified visual findings are triaged for priority viewing by a healthcare professional (e.g., radiologist, emergency room physician), for example, by ranking according to a priority score, for example, probability of the respective image having the visual finding. For example, images likely having pneumothorax visual findings are prioritized, optionally according to computed probability of having the pneumothorax visual finding. The triage system enables rapid diagnosis of pneumothorax, which leads to rapid treatment of the pneumothorax, saving the patient from complication of delayed treatment of pneumothorax and/or missing the pneumothorax entirely. The triage system is enabled, at least due to the trained single-label neural network described herein that computes the likelihood of a single visual finding type being depicted in the target anatomical image.

At least some of the systems, methods, apparatus, and/or code instructions described herein improve neural network technology, by improving the process of selecting an ensemble from multiple instances of a trained neural network, where each instance varies by neural network parameter(s) (e.g., input image size, normalization, mean, and architecture variations, as described herein). The ensemble is selected from instances of the single-label neural network that were trained using the two step process described herein, i.e., fine tuned and/or re-trained using the trained multi-label neural network as baseline. Each instance is a variation of the single-label neural network in terms of one or more neural network parameters (as described herein). Since each instance is trained to perform the same task of determining likelihood of the single visual finding type being depicted in the target anatomical image, and since each trained instance of the single-label neural network varies in terms of neural network parameters, the performance of each instance varies. The ensemble is selected to identify the combination of instances that provide the overall best performance in terms of determining likelihood of the single visual finding type being depicted in the target anatomical image.

Using standard processes, a standard AUC metric measures the entire area under the ROC for computing a metric indicative of performance of a certain trained neural network. However, Inventors discovered that the standard process using AUC provides a general overall performance metric, which does not necessarily reflect desired target sensitivity and/or target specificity. For example, a certain trained neural network may have excellent overall performance, but does not perform sufficiently well (and/or has lower performance) at the target sensitivity and/or target specificity. In contrast, another trained neural network may have lower overall performance, but has excellent performance at the target sensitivity and/or target specificity. Measuring the entire area using standard AUC metrics is less informative. In contrast, the selection process enabled by the mini-AUC code described here is based on a more focused area of the ROC defined by the target sensitivity and/or target specificity. Given a target sensitivity and optionally a tolerance, the area under the graph for the defined region is measured. The area under the graph for the defined region is used to select the members of the ensemble rather than the entire area as done using standard techniques. The mini-AUC process is used to select the members of the ensemble based on a target sensitivity and/or target specificity within a tolerance requirement. The working point, and/or threshold (for determining whether the respective is positive or negative for depicting the desired single visual finding type) are selected according to having at least a minimal value of the target sensitivity and/or according to a highest value of the target specificity. For example, the minimum target sensitivity may be set as 90% with a tolerance of 2%. The corresponding maximum specificity may be identified.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
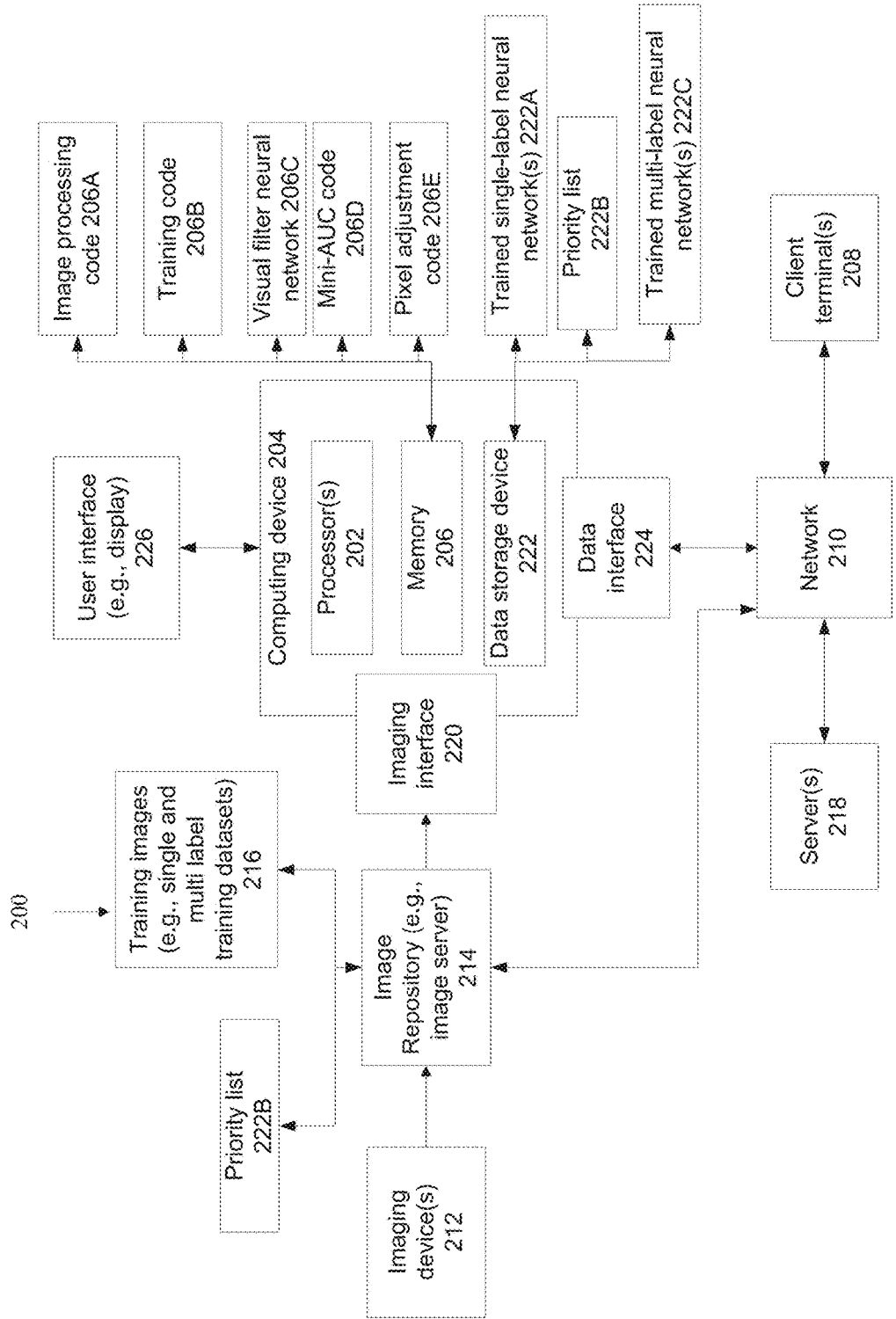
FIG. 2 is a block diagram of a system for training a single-label neural network for detection of a single visual finding type from a baseline of a multi-label neural network, and/or for analyzing anatomical images using the single-label neural network, optionally to create a priority list, in accordance with some embodiments of the present invention.
Figure 3:
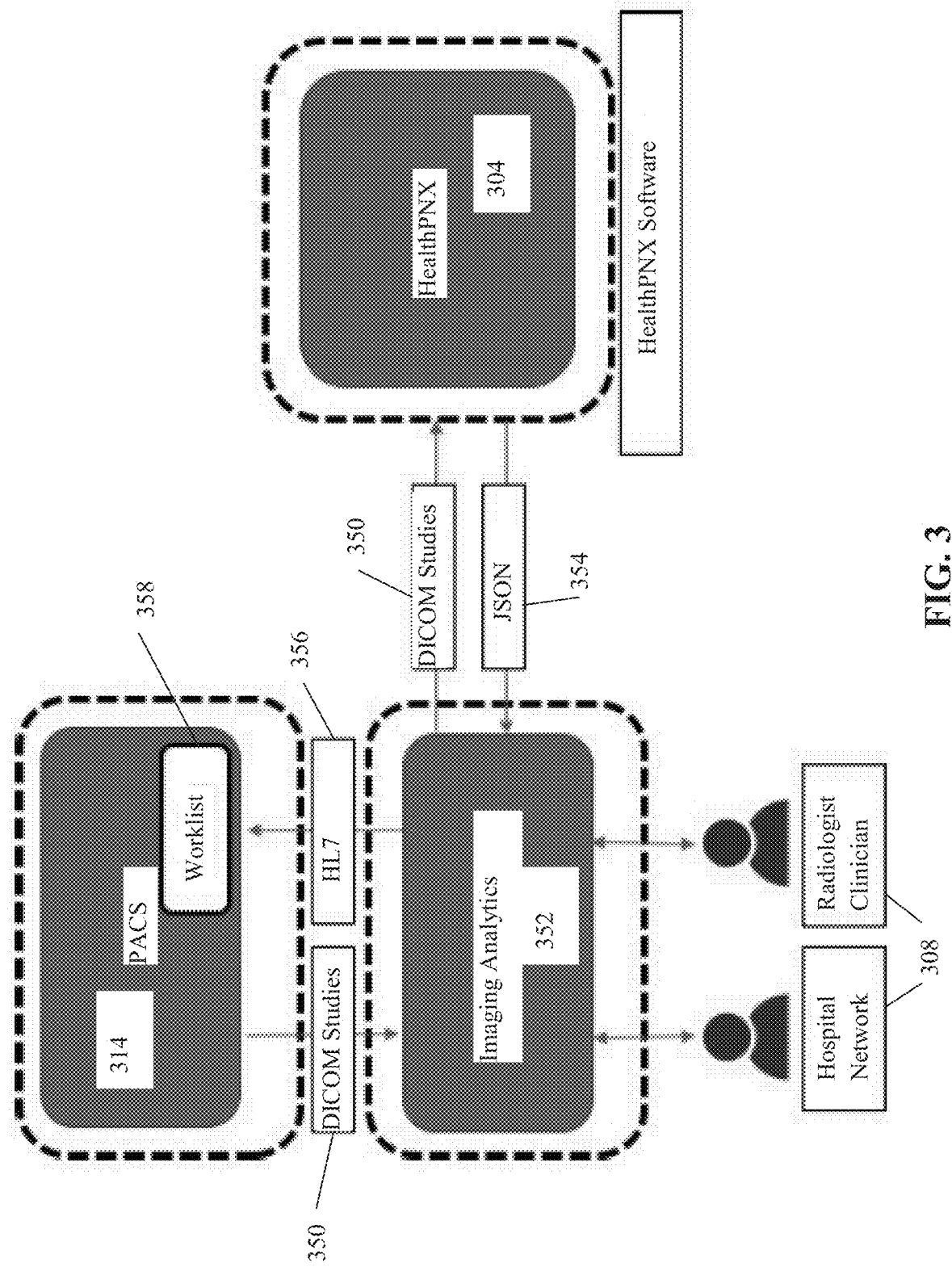
FIG. 3 is a dataflow diagram depicting exemplary dataflow for detection of an indication of a single visual finding type in a target anatomical image of a target individual by a single-label neural network trained from a baseline of a multi-label neural network, and optionally creating a priority worklist, in accordance with some embodiments of the present invention.
Figure 4:
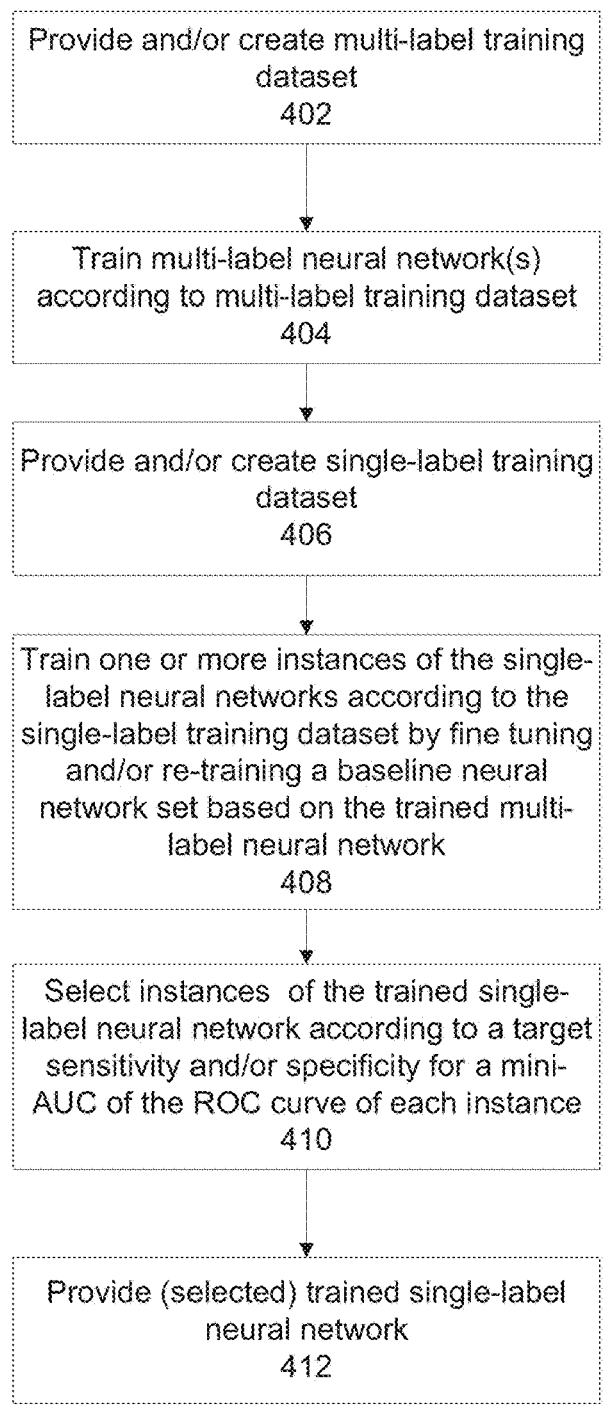
FIG. 4 is a flowchart of a process for training the single-label neural network from the multi-label neural network, in accordance with some embodiments of the present invention.

Reference is now made to FIG. 1, which is a flowchart of a method for detection of an indication of a single visual finding type in a target anatomical image of a target individual by a single-label neural network trained from a baseline of a multi-label neural network that include multiple visual finding types including the selected single visual finding type, in accordance with some embodiments of the present invention. Reference is also made to FIG. 2, which is a block diagram of a system 200 for training a single-label neural network 222A for detection of a single visual finding type from a baseline of a multi-label neural network 222C that include multiple visual finding types including the selected single visual finding type, and/or for analyzing anatomical images using the single-label neural network, optionally to create a priority list 222B, in accordance with some embodiments of the present invention. Reference is also made to FIG. 3, which is a dataflow diagram depicting exemplary dataflow for detection of an indication of a single visual finding type in a target anatomical image of a target individual by a single-label neural network trained from a baseline of a multi-label neural network that include multiple visual finding types including the selected single visual finding type, and optionally creating a priority worklist, in accordance with some embodiments of the present invention. Reference is also made to FIG. 4, which is a flowchart of a process for training the single-label neural network from the multi-label neural network, in accordance with some embodiments of the present invention.

System 200 may implement the acts of the method described with reference to FIG. 1 and/or FIG. 3 and/or FIG. 4, optionally by a hardware processor(s) 202 of a computing device 204 executing code instructions stored in a memory 206.

An exemplary implementation of an x-ray triage system is now described to help understand system 200. In a busy emergency room, many chest x-rays of different patients are captured by imaging device 212 and stored in a PACS server 214. Computing device computes a likelihood of each chest x-ray depicting a single visual finding type denoting pneumothorax by trained a single-label neural network 222A. Single-label neural network 222A is computed from multi-label neural network 222C using a respective multi-label training dataset and a single-label training dataset, as described herein. The performance of single-label neural network in terms of target sensitivity and/or target specificity may be obtained by mini-AUC code, as described herein. Prior to computation by single-label neural network 222A, each chest x-ray may be processed by visual filter neural network code 206C for exclusion of irrelevant images (e.g., non-chest x-rays, and/or non-x-ray images and/or non AP-PA images). The chest x-ray images (before or after filtering) may be further processed for removal of outlier pixel intensity values and/or adjusting pixel intensity values by executing pixel adjustment code 206E. Additional details of removing outlier pixel intensity values and/or adjusting pixel intensity values are described with reference to co-filed application Ser. No. 16/696,619. The system provides a triage of the anatomical images, by generating a priority worklist 222B. The worklist 222B is generated by ranking the chest x-rays according to a priority score computed based on the likelihood. The higher the probability that a certain chest x-ray has a visual finding indicating pneumothorax, the higher the ranking on the worklist. A healthcare practitioner (e.g., radiologist, ER physician) checks the worklist 222B, and reviews the anatomical images on a display of client terminal 208, for the presence of pneumothorax, starting from the top. The healthcare practitioner is directed to the most urgent chest x-rays most likely to have a visual finding indicative of pneumothorax, reducing the time to diagnose and treat the patient for the pneumothorax in comparison to standard systems that do not provide the triage feature. Patients determined to have pneumothorax may be treated by a physician to remove the excess air.

Computing device 204 may be implemented as, for example, a client terminal, a server, a virtual server, a radiology workstation, a virtual machine, a computing cloud, a mobile device, a desktop computer, a thin client, a Smartphone, a Tablet computer, a laptop computer, a wearable computer, glasses computer, and a watch computer. Computing 204 may include an advanced visualization workstation that sometimes is add-on to a radiology workstation and/or other devices for presenting indications of the visual finding type to the radiologist.

Computing device 204 may include locally stored software that performs one or more of the acts described with reference to FIG. 1 and/or FIG. 3 and/or FIG. 4, and/or may act as one or more servers (e.g., network server, web server, a computing cloud, virtual server) that provides services (e.g., one or more of the acts described with reference to FIG. 1 and/or FIG. 3 and/or FIG. 4) to one or more client terminals 208 (e.g., client terminal used by a user for viewing anatomical images, remotely located radiology workstations, remote picture archiving and communication system (PACS) server, remote electronic medical record (EMR) server) over a network 210, for example, providing software as a service (SaaS) to the client terminal(s) 208, providing an application for local download to the client terminal(s) 208, as an add-on to a web browser and/or a medical imaging viewer application, and/or providing functions using a remote access session to the client terminals 208, such as through a web browser.

Client terminal(s) 208 may be implemented as, for example, a radiology workstation, a desktop computer (e.g., running a PACS viewer application), a mobile device (e.g., laptop, smartphone, glasses, wearable device), and nurse station server.

Is it noted that the training of the single-label neural network and multi-label neural network, and the application of the trained single-label neural network to anatomical images to compute likelihood of visual finding types, may be implemented by the same computing device 204, and/or by different computing devices 204, for example, one computing device 204 trains the multi-label neural network and single-label neural network, and transmits the trained single-label neural network to a server device 204.

Computing device 204 receives 2D images, and/or 2D slices (optionally extracted from 3D imaging data) captured by an anatomical imaging device(s) 212, for example, an x-ray machine, a magnetic resonance imaging (MRI) device, a computer tomography (CT) machine, and/or an ultrasound machine. Anatomical images captured by imaging machine 212 may be stored in an image repository 214, for example, a storage server (e.g., PACS server), a computing cloud, virtual memory, and a hard disk. The anatomical images stored by image repository 214 may include images of patients optionally associated with text based radiology reports. Training images 216 are created based on the captured anatomical images and text based radiology reports, as described herein.

Training images 216 may include (and/or be used to create) the multi-label training dataset for training the multi-label neural network, and/or single-label training dataset for training the single-label neural network, as described herein. As used herein, the term training images and training dataset (i.e., single and/or multi-label) may be interchanged. It is noted that training images 216 may be stored by a server 218, accessibly by computing device 204 over network 210, for example, a publicly available training dataset, and/or a customized training dataset created for training the multi-label neural network and/or the single-label neural network, as described herein.

Anatomical images captured by imaging machine(s) 212 depict internal anatomical features and/or anatomical structures within the body of the target patient.

Exemplary anatomical images include 2D x-ray images captured by an x-ray machine. Exemplary x-ray anatomical images include: AP and PA views of the chest, abdominal x-rays, and x-rays of limbs. Selected views of the x-ray images may be defined as the best view for detecting the visual finding type.

Computing device 204 may receive the anatomical images for computation of the likelihood of depicting the visual finding type, and/or receive training images 216 (e.g., single and/or multi label training dataset, or create the single and/or multi label training datasets from the training images), from imaging device 212 and/or image repository 214 using one or more imaging interfaces 220, for example, a wire connection (e.g., physical port), a wireless connection (e.g., antenna), a local bus, a port for connection of a data storage device, a network interface card, other physical interface implementations, and/or virtual interfaces (e.g., software interface, virtual private network (VPN) connection, application programming interface (API), software development kit (SDK)).

Hardware processor(s) 202 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 202 may include one or more processors (homogenous or heterogeneous), which may be arranged for parallel processing, as clusters and/or as one or more multi core processing units.

Memory 206 (also referred to herein as a program store, and/or data storage device) stores code instruction for execution by hardware processor(s) 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). For example, memory 206 may store image processing code 206A that implement one or more acts and/or features of the method described with reference to FIGS. 1 and/or 3, and/or training code 206B that execute one or more acts of the method described with reference to FIG. 4, and/or code instructions of trained single-label neural network 222A and/or code of multi-label neural network 222C and/or visual filter neural network code 206C for filtering the anatomical images prior to processing by the trained single-label neural network and/or prior to being used for training the single-label and/or multi-label neural network and/or mini-AUC code 206D for selecting single-label neural networks according to a target sensitivity and/or specificity and/or pixel adjustment code 206E for adjusting pixel intensity values for removal of outliers, as described herein. Additional details of the visual filter neural network 206C are described with reference to co-filed application Ser. No. 16/696,619, co-filed with the present application.

Alternatively or additionally, client terminal(s) may locally store and/or execute image processing code 206A, visual filter neural network 206C, and/or code instructions of trained single-label neural network 222A and/or code of multi-label neural network 222C and/or priority list 222B and/or mini-AUC code 206D and/or pixel adjustment code 206E.

Computing device 204 may include a data storage device 222 for storing data, for example, code instructions of trained single-label neural network 222A and/or code of multi-label neural network 222C (as described herein), priority list 222B (generated as described herein), visual filter neural network 206C, mini-AUC code 206D, and/or training images 216, and/or text based radiology reports (for creating the multi-label training dataset and/or single-label training dataset, as described herein). Data storage device 222 may be implemented as, for example, a memory, a local hard-drive, a removable storage device, an optical disk, a storage device, and/or as a remote server and/or computing cloud (e.g., accessed over network 210). It is noted code instructions of trained single-label neural network 222A, code of multi-label neural network 222C, visual filter neural network 206C, training images 216, priority list 222B, mini-AUC code 206D and/or pixel adjustment code 206E and/or text based radiology reports may be stored in data storage device 222, with executing portions loaded into memory 206 for execution by processor(s) 202.

Optionally, priority list 222B is provided to image server 214, for example, for instructing the priority presentation of images stored by image server 214. Alternatively or additionally, computing device 204 provides instructions for image server 214 to generate priority list 222B.

Computing device 204 may include data interface 224, optionally a network interface, for connecting to network 210, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 204 may access one or more remote servers 218 using network 210, for example, to download updated training images 216 and/or to download an updated version of image processing code, training code, visual filter neural network code, the trained single-label neural network, and/or trained multi-label neural network.

It is noted that imaging interface 220 and data interface 224 may be implemented as a single interface (e.g., network interface, single software interface), and/or as two independent interfaces such as software interfaces (e.g., as application programming interfaces (API), network ports) and/or hardware interfaces (e.g., two network interfaces), and/or combination (e.g., single network interface, and two software interfaces, two virtual interfaces on a common physical interface, virtual networks on a common network port). The term/component imaging interface 220 may sometimes be interchanged with the term data interface 224.

Computing device 204 may communicate using network 210 (or another communication channel, such as through a direct link (e.g., cable, wireless) and/or indirect link (e.g., via an intermediary computing device such as a server, and/or via a storage device) with one or more of:

Client terminal(s) 208, for example, when computing device 204 acts as a server that computes likelihood of the visual finding in anatomical images, provides the image storage server with the computed likelihood for determining a priority score of the respective anatomical image for creating the priority list, and where the highest ranked anatomical images are viewed on a display of the client terminal 208.

Server 218. In one implementation, server 218 is implemented as image server 214, for example, a PACS server. Server 218 may store new anatomical images as they are captured, and/or may store the training dataset. Server 214 may store and/or generate priority list 222B. In another implementation, server 218 is in communication with image server 214 and computing device 204. Server 218 may coordinate between image server 214 and computing device 204, for example, transmitting newly received anatomical images from server 218 to computing device 204 for computation of likelihood of having a visual finding (by single-label training dataset 222A as described herein), and transmitting an indication of the computed likelihood from computing device 204 to server 218. Server 218 may compute priority scores and/or rank the anatomical images according to the computed likelihood for computing the priority list. Server 218 may send a list of priority ranked anatomical images and/or the priority list to image server 214, optionally for presentation to a healthcare provider on the display of the client terminal. Client terminal 208 may access the anatomical images of the priority list via server 218, which obtains the images from image server 214. Alternatively, one or more of the described functions of server 218 are performed by computing device 204 and/or imager server 214.

Anatomical image repository 214 that stores anatomical images and/or imaging device 212 that outputs the anatomical images.

Computing device 204 includes or is in communication with a user interface 226 that includes a mechanism designed for a user to enter data (e.g., patient data) and/or view the indications of identified visual findings. Exemplary user interfaces 226 include, for example, one or more of, a touchscreen, a display, a keyboard, a mouse, and voice activated software using speakers and microphone.

Reference is now made to FIG. 3, which is a schematic 300 depicting exemplary dataflow for detection of an indication of a single visual finding type in a target anatomical image of a target individual by a single-label neural network trained from a baseline of a multi-label neural network, in accordance with some embodiments of the present invention. A data storage server 314, for example, a PACS server, provides anatomical images 350 to an Imaging Analytics process 352. Data storage server 314 may correspond to image repository and/or image server 214 described with reference to FIG. 2. Anatomical images 350 may be DICOM® studies, for example, chest x-ray images, abdominal x-ray limb x-rays, and CT scans (i.e., of chest, abdomen and/or limbs). Imaging Analytics process 352 may be implemented as, for example, a server, a process executing on data storage server 314, corresponding to server 218 of FIG. 2, and/or corresponding to computing device 204. Imaging analytics process 352 provides anatomical images 350 to HealthPNX process 304. HealthPNX process 304 may correspond to computing device 204 of FIG. 2, and/or be implemented as a process executing on PACS server 314 and/or on the image analytics server. HealthPNX process 304 computes the likelihood of each anatomical image (e.g., x-ray) depicting a visual finding type, for example, indicative of pneumothorax. The computation of the likelihood of the visual finding type is computed by the trained single-label neural network, as described herein. Optionally, each x-ray is first processed by the visual filter neural network (as described herein) for exclusion of irrelevant images, prior to computation by the single-label neural network. HealthPNX process 304 sends an indication of the computed likelihood of visual finding 354 to imaging analytics process 352, for example, formatted in JSON. Imaging analytics process 352 may reformat the indication of the computed likelihood of visual finding into another protocol 356 (e.g., HL7) for providing to PACS 314. The anatomical images are arranged into a worklist 358 (corresponding to priority list 222B described with reference to FIG. 2) according to the computed likelihood of visual finding type, for example, ranked in decreasing order according to a ranking score computed based on the computed likelihood of visual finding. For example, ranked according to probability of the respective x-ray depicting the visual finding type indicative of pneumothorax. The anatomical images are accessed for manual review according to worklist 358 by a healthcare provider (e.g., hospital worker, radiologist, clinician) via a client terminal 308. The anatomical images are triaged for review by the healthcare provider according to the most urgent cases, most likely to include the visual finding, for example, pneumothorax, enabling rapid diagnosis and treatment of the acute cases. Patients diagnosed with pneumothorax may be rapidly treated, preventing or reducing complications and/or morbidity resulting from a delay in diagnosis and a delay in treatment.

Referring now back to FIG. 1, at 102, the single-label neural network(s) is trained and/or provided.

The trained single-label neural network is fed a target anatomical image, and outputs an indication of likelihood (e.g., absolute indication thereof, and/or probability value) of the single visual finding type being depicted in the target anatomical image.

An exemplary process of training the single-label neural network is described with reference to FIG. 4.

The single-label neural network is computed by fine-tuning and/or retraining a trained multi-label neural networking according to a single-label training dataset of anatomical images labeled with an indication of the visual finding type. The multi-label neural network is trained to compute likelihood (e.g., absolute indication thereof, and/or probability value) of each of multiple visual finding types based on a multi-label training dataset of anatomical images labeled with the multiple visual finding types.

The accuracy of the trained single-label neural network for detection of the single visual finding type in the target anatomical image may be higher than the accuracy of the multi-label neural network for detection of the single visual finding type in a target anatomical image, and/or may be higher than another single-label neural network trained only on the single-label training dataset using a standard untrained neural network as the initial baseline, and/or may be higher than another single-label neural network trained on a multi-object neural network trained to detect non-medical objects in non-medical images (e.g., ImageNet).

Multiple single-label neural networks may be trained and/or provided. Each single-label neural network may be trained to detect a respective unique visual finding type when fed the same anatomical image outputted by a target anatomical imaging modality depicting a target body region at a target sensor viewing angle. For example, one single-label neural network detects pneumothorax in AP and/or PA and/or lateral chest x-rays, and another single-label neural network detects pneumomediastinum in the AP and/or PA chest x-rays. Alternatively or additionally, each single-label neural network may be trained to detect a unique visual finding type according to a certain anatomical image outputted by a certain anatomical imaging modality depicting a certain body region at a certain sensor viewing angle. For example, one single-label neural network detects pneumothorax in AP and/or PA and/or lateral chest x-rays, and another single-label neural network detects pneumoperitoneum in supine abdominal x-rays, and/or AP/PA chest x-rays.

When multiple single-label neural network are used that accept anatomical images of different imaging modalities and/or different sensor angles and/or different body types, one or more visual filter neural networks may exclude inappropriate anatomical images from being fed into the respective single-label neural network and/or may select appropriate anatomical image for feeding into the respective single-label neural network.

Exemplary types of anatomical images fed into the single-label neural network and resulting output of likelihood of the single visual finding type being depicted in the respective image include: two dimensional (2D) AP and/or PA and/or lateral chest x-ray for detecting pneumothorax including a small pneumothorax, 2D AP and/or PA chest x-ray for detecting pneumomediastinum, 2D abdominal x-ray at a side-view for detecting pneumoperitoneum, one or more x-rays of bones and/or joints captured at one or more sensor orientations to detect fracture, and US images of the appendix for detecting acute appendicitis.

At 104, one or more anatomical images are received, for example, from a PACS server, an EMR server, from the anatomical imaging device, and/or from a storage device (e.g., portable storage medium, storage server). The images may be obtained one at a time, for example, as the anatomical images are captured and stored, and/or may be obtained as a batch, for example, all images captured in the last 15 minutes.

The images may be captured from different anatomical imaging modality machines, and/or captured at different sensor orientations.

Exemplary anatomical imaging device includes an x-ray machine that captures a two dimensional anatomical image.

The anatomical images may be, for example, 2D images (e.g., x-ray, ultrasound) and/or 2D slices of 3D images (e.g., of CT and/or MRI scans).

Anatomical images may be stored as single images, a series of multiple independent images, and/or set of slices (e.g., 2D slices of a 3D volume image). Optionally, each one of the anatomical images is fed into the neural network(s), as described herein.

At 106, the anatomical images are fed into one or more visual filter neural network(s) 206C.

Optionally, each visual filter neural network excludes anatomical images that are inappropriate for the corresponding target single-label neural network, in terms of images that are captured by another imaging modality and/or images depicting another body part and/or images captured by another sensor orientation angle. For example, for a single-label neural network that processes AP and/or PA chest x-rays, non-chest x-rays are excluded, and other sensor orientations (i.e., non-AP and non-PA) are excluded.

Optionally, each single-label neural network has its own corresponding visual filter neural network, trained according to the image requirements of the corresponding single-label neural network. Alternatively, a single visual filter neural network is trained for multiple different single-label neural networks, for example, outputting a label for the fed image indicative of anatomical imaging modality and/or body type and/or sensor orientation. The labels may be used to feed the images to the relevant single-label neural networks.

The visual filter neural network may detect rotated anatomical images, optionally an amount of rotation relative to baseline (e.g., 90 degrees, 180 degrees, 270 degrees). The rotated anatomical images may be rotated back to baseline.

The target anatomical image(s) are fed into the visual filter neural network for outputting a classification category indicative of a target body region depicted at a target sensor orientation and a rotation relative to a baseline defined by the single-label neural network (e.g., AP/PA chest x-ray), or another classification category indicative of at least one of a non-target body region and a non-target sensor orientation (e.g., non-chest, non-AP/PA, non-x-ray). A sub-set of the target anatomical images classified into the another classification category are rejected, to obtain a remaining sub-set of the target anatomical images. The remaining sub-set of the target anatomical images classified as rotated relative to the baseline, are rotated to the baseline, to create a set of images which are all at baseline.

Additional details of training and using the visual filter neural network(s) are described with reference to co-filed application Ser. No. 16/696,619, which is co-filed with the present application, and is incorporated herein by reference in its entirety.

Optionally, images are processed to remove outlier pixel intensity values and/or adjust the pixel intensity values. The outlier pixel intensity values may denote injected content, for example, metadata text overlaid on the real image, for example, the name of the patient, and an indication of the side of the patient (e.g., L for left side) and/or additional data of the study (e.g., AP chest x-ray). The injected content is removed and/or adjusted by adjusting the intensity of the pixels thereof. Briefly, pixels for the target anatomical image having outlier pixel intensity values denoting an injection of content are identified. The outlier pixel intensity values of the identified pixels are adjusted to values computed as a function of non-outlier pixel intensity values. The processing of the image may be performed prior to being fed into the visual filter neural network and/or for the images that passed through the visual filter neural network (i.e., non-rejected). Additional details of performing the removal of the outlier pixel intensity values and/or adjustment of pixel intensity values are described with reference to co-filed application Ser. No. 16/696,619.

At 108, the target anatomical image(s) are fed into the single-label neural network.

Optionally, when the visual filter neural network is implemented, the anatomical images(s) fed into the single-label neural network include the anatomical images selected by the visual filter and/or excludes anatomical images rejected by the visual filter, and/or includes anatomical images rotated to baseline based on output of the visual filter.

Optionally, when the pixel adjustment code is implemented, the anatomical image(s) are processed to remove injected content and/or adjust pixel intensity value of the pixels denoting injected content and/or other pixels (i.e., not denoting injected content).

Optionally, when the single-label neural network comprises an ensemble of neural networks, the target anatomical image(s) is fed into each one of the neural networks of the ensemble. Optionally, multiple instances of the target anatomical image(s) is created, by pre-processing the target anatomical image(s) according to input requirements of the respective neural network of the ensemble. Input requirements of the neural networks of the ensemble may differ according to neural network parameters described herein, for example, image size (i.e., scaling the image to the required image size), center-crop (e.g., center area of the image, given by the corresponding neural network of the ensemble's input size is extracted out), mean normalization (e.g., mean of the pre-cropped image is subtracted), and standard deviation normalization (e.g., the standard deviation of the pre-cropped image is divided by).

At 110, a likelihood of an indication of the single visual finding type being depicted in the target anatomical image is outputted and/or computed by the single-label neural network.

The single visual finding type denoting an acute medical condition for early and rapid treatment thereof, for example, pneumothorax, pneumomediastinum, pneumoperitoneum, and fracture. Such visual findings tend to be fine features and therefore difficult to identify on x-ray, especially in early stages and/or when the radiologist is looking for other multiple visual findings. However, the visual finding types are indicative of an acute medical condition that is progressive, requiring early and rapid treatment to reduce risk of complications. A delay in treatment may result in patient morbidity and/or mortality that may otherwise have been prevented or reduced by early treatment.

Optionally, the likelihood is represented as an absolute value, optionally a single indication or a binary indication, for example, present, or not present. Alternatively or additionally, the computed likelihood denotes a confidence score indicative of probability of the visual finding type being depicted in the anatomical image.

At 112, when multiple anatomical images are fed into the single-label neural network, instructions for creating a triage list may be generated, and/or the triage list may be generated. The triage list includes anatomical images determined as likely to depict the single visual finding type. Optionally, the triage list is ranked by decreasing likelihood of the indication of the visual finding type based on the confidence score. For example, images having a higher computed probability score of depicting the visual finding type are ranked higher in the list than other images having lower probability scores.

As used herein, the term priority list and triage list are interchangeable.

The triage list is for manual review by a human user (e.g., radiologist, emergency room physician, surgeon) of respective target anatomical images computed as likely depicting the indication of the visual finding type.

The priority list may be created by the computing device, and provided to image server, and/or the client terminal. In another implementation, the computing device provides instructions for creating the priority list to the image server, and the image server crates the priority list.

The list may be viewed by the user (e.g., within the PACS viewer) optionally for manual selection of images for viewing, and/or may define automatic sequential loading of images for viewing by the user (e.g., within the PACS viewer).

At 114, the user may manually view images in the priority list, optionally according to the ranking.

At 116, the acute medical condition may be diagnosed in the patient. The visual finding type is a sign of the acute medical condition. The patient may be treated for the acute medical condition.

For example, when the visual finding type of pneumothorax is found in the chest x-ray by the single-label neural network, and the finding is confirmed by manual visual inspection by a radiologist, the patient may be diagnosed and/or treated, for example, by insertion of a needle or chest tube to remove the excess air.

Referring now back to FIG. 4, at 402, a multi-label training dataset is provided and/or created.

The multi-label training dataset includes multiple anatomical images each associated with a label indicative of one or more defined visual finding types, or indicative of no visual finding types (i.e., explicit indication, or implicit indication by lack of a label of visual finding type(s)).

Optionally, the images stored in the multi-label training dataset have been processed by one or more visual filter neural networks, for exclusion of irrelevant images (e.g., of a different body region and/or different sensor orientation and/or different imaging modality) and/or for rotating rotated images back to baseline.

Optionally, images may be preprocessed to increase the number of training images and/or variety of the training image, for example, with the following additional augmentations: random horizontal flip, random crop, random rotation, and random zoom.

Exemplary visual finding types defined for AP and/or PA and/or lateral chest x-rays include: abnormal aorta, aortic calcification, artificial valve, atelectasis, bronchial wall thickening, cardiac pacer, cardiomegaly, central line, consolidation, costrophrenic angle blunting, degenerative changes, elevated diaphragm, fracture, granuloma, hernia diaphragm, hilar prominence, hyperinflation, interstitial markings, kyphosis, mass, mediastinal widening, much bowel gas, nodule, orthopedic surgery, osteopenia, pleural effusion, pleural thickening, pneumothorax, pulmonary edema, rib fracture, scoliosis, soft tissue calcification, sternotomy wires, surgical clip noted, thickening of fissure, trachea deviation, transplant, tube, and vertebral height loss.

Optionally, the multi-label training dataset stores images of a same body region, captured by a same imaging modality time, having a same sensor orientation. For example, AP and/or PA chest x-rays. As used herein, AP and PA may be considered as having the same sensor orientation.

Multiple multi-label training datasets may be created, for example, for different body parts and/or different imaging modality types and/or different sensor orientations.

An exemplary process for creating labels for the anatomical images indicative of the visual finding types depicted therein is now described. Additional details of an exemplary process of creating the labels for the multi-label training dataset from text based radiology report is described with reference to Provisional patent application Ser. No. 15/972,912.

Optionally, labels of the anatomical images of the multi-label training dataset are created based on an analysis that maps individual sentences of a respective text based radiology report to a corresponding visual finding type of multiple defined visual finding types. The text based radiology report includes a description of the radiological reading of the images, for example, typed by radiologist, or transcribed from a verbal dictation provided by the radiologist. The sets of anatomical images and associated radiology report may be obtained, for example, from a PACS server, and/or EMR records of the sample individuals.

Optionally, a respective tag is created for each set of anatomical images of each sample individuals. Each tag includes one or more visual findings depicted in one or both of the images. The tags may be implemented as, for example, a metadata tags, electronic labels, and/or pointers to entries in a dataset (e.g., an array where each element denotes a distinct visual findings).

The tags may be created according to an analysis that maps individual sentences of each respective radiology report to corresponding indications of distinct visual findings types depicted in the anatomical images associated with the respective radiology report. An individual sentence is mapped to one of the distinct visual finding types.

A set of distinct visual findings types may be created according to an analysis of the sentences (optionally all sentences) of the radiology reports of the images. The indications of distinct visual finding types are based on visual finding types that are identified by radiologists. However, since different radiologists may use different sentences and/or different terms to refer to the same visual finding, multiple different sentences may map to the same distinct visual finding.

Optionally, the individual sentences from the radiology reports of the sample individuals are clustered into a relatively small number of distinct visual finding types, for example, about 10 visual finding types, or about 20, or about 25, or about 30, or about 40, or about 50, or about 100. The number of radiology reports is small in comparison to the number of distinct sentences, for example, about 500,000, or about 1 million sentences. Each cluster denotes one of the distinct visual finding. All sentences within the respective cluster are indicative of same respective distinct visual finding.

The clustering may be performed, for example, manually by users, and/or based on supervised and/or unsupervised machine learning methods that are designed to create clusters.

Clustering may be performed according to one or more of the following:

1. Manually going over some of the more-frequent sentences and tagging them (e.g., as described in the experiment in the Examples section).

2. Using algorithm(s) to automatically parse sentences in the reports and associate them to positive findings (or negative).

3. The algorithm(s) in (2) may be rule-based (e.g., for each finding, a human writes a formula, and if the sentence satisfies this formula, the sentence is mapped to a positive indication of the finding).

4. The algorithm(s) in (2) may learn the formula automatically (i.e. ML algorithm) given a sample of manually annotated sentences (such as the ones in (1)).

One or more training datasets may be created for training one or more multi-label neural network. Each training dataset includes sets of anatomical images and associated tags.

The training datasets may be sorted according to the target multi-label neural network being trained, for example, according to body portion being imaged, according to image modality, and/or according to sensor orientation.

Optionally, the training dataset is created by mapping a sub-set of sentences of the text based radiology reports (optionally one or more sentences from each report) of the sample individuals that are indicative of positive findings (i.e., a visual finding type which may be abnormal) to one of the indications of visual finding types. The negative sentences are either ignored, or mapped to negative labels for the mentioned visual finding types in the sentence. The neutral sentences are just ignored, as they convey no indicative information. The ambiguous sentences may lead to the removal of the associated set of images from the training set.

In another example, another sub-set of sentences denoting negative findings (e.g., normal findings, or lack or abnormal finding), and/or neutral data (i.e., does not indicate a positive or negative finding), and/or ambiguous data (e.g., unclear whether the data indicates a positive or negative finding) is mapped to another tag indicative of no visual finding types. The other sub-set of sentences are not mapped to any one of the indications of visual findings. The multi-label neural network may be trained on both sub-sets of sentences and associated anatomical images, where one sub-set trains the multi-label neural network to identify the visual finding types, and/or the other sub-set trains the multi-label neural network to avoid false positives by incorrectly designating negative finding as visual finding types.

Sentences denoting neutral findings may be ignored.

Optionally, a fully covered training dataset is created according to a sub-set of the text based radiology reports of the sample individuals (i.e., some reports are excluded from the training dataset). For each respective text based radiology report included in the sub-set, each one of the sentences of the respective text based radiology report is mapped to one of: one of the indications of visual finding types (i.e., denoting a positive finding from the findings supported by the model), a negative finding, and neutral data. The multi-label neural network may be trained according to the fully covered training dataset and associated anatomical images.

Alternatively, any hit training dataset is created according to a sub-set of the text based radiology reports of the sample individuals (i.e., some reports are excluded from the training dataset). For each respective text based radiology report included in the sub-set, at least one of the sentences of the respective text based radiology report is mapped to one of the indications of visual finding types. Sentences mapping to negative findings and/or neural data are ignored. The multi-label neural network may be trained according to the any hit training dataset and associated anatomical images.

Optionally, a prevalence of the anatomical images labeled with the single visual finding type stored in the multi-label training dataset is statistically significantly higher than a prevalence of the anatomical images labeled with the single visual finding type stored in the storage server and/or prevalence of patients with pneumothorax in practice (e.g., prevalence in the emergency room, prevalence in anatomical images, prevalence in the general population). For example, as described in the experiment section, the multi-label training dataset may include 5828 images depicting pneumothorax, and 2,043,625 images not depicting pneumothorax, which may be representative of the wild prevalence of pneumothorax in patients undergoing chest x-ray imaging. The prevalence of the images depicting pneumothorax in the multi-label training dataset is set to be much higher, for example, about 33% of all images, or about 50%, or about 25-50%, or other values. The higher prevalence may increase the accuracy of the trained multi-label neural network in detecting the visual finding type indicative of pneumothorax. The higher prevalence of images depicting pneumothorax may be obtained, for example, by arranging the training images in 3 cyclic queues: "positive", "normal", and "abnormal", optionally each set at ⅓ of the total images, or other distributions may be used. An image is added to the multi-label training batch queue by being drawn uniformly at random, and then the next image for training the multi-label neural network is obtained from that queue. Hence each batch contains, on average, 33% positive images.

At 404, one or more multi-label neural networks are trained for detection of one or more of the visual finding types in a target anatomical image, according to the multi-label training dataset. Optionally, the multi-label neural network is trained to identify about 20-50 different visual finding types.

Optionally, the multi-label neural network is trained from scratch from a template neural network. The template neural network may be an off-the-shelf publicly available neural network, for example, DenseNet121, ResNet152, Inception-v4, and Inception-v3.

Optionally, the multi-label neural network is trained using a categorical cross-entropy loss function.

Optionally, the validation loss of the single visual finding type is monitored during the training of the multi-label neural network (which is trained to detect a large number of visual finding types, for example, about 40 types) to determine when the validation loss of the single visual finding type has stabilized. Alternatively or additionally, during training of the multi-label neural network to detect the multiple types of visual findings, the validation loss of the multi-label neural network for the selected single visual finding type is monitored to detect a checkpoint of the neural network that had the lowest validation loss. Multiple instances of the multi-label neural network may be trained, each varying in terms of one or more neural network parameters. The instance of the multi-label neural network that obtained the lowest validation loss for the selected single visual finding type is designated for use for training the single-label neural network, as described herein. The single-label neural network is trained to directly minimize the loss for the selected single visual finding type, as described herein.

The stabilizing denotes that the ability of the multi-label neural network to detect the presence of the single visual finding type in a target anatomical image has peaked. The baseline neural network for training of the single-label neural network to detect the single visual finding type is set according to a checkpoint of network weights of the multi-label neural network when stabilization of the validation loss is determined.

One of the instances may be selected according to a validation loss of the selected single visual finding type. When the single-label neural network is trained, the single-label neural network is initialized with a checkpoint of network weights of the selected instance of the multi-label neural network.

At 406, a single-label training dataset is provided and/or created.

The single-label training dataset includes anatomical images each associated with a label indicative of the selected single visual finding type, and optionally alternatively a label indicative of an absence of the single visual finding type.

Multiple single-label training dataset may be provided and/or created, for example, for each distinct visual finding type and/or distinct body region depicted in the anatomical image and/or distinct sensor orientation and/or distinct imaging modality.

It is noted that the single visual finding type is selected from the multiple visual findings types which are used to create the multi-label training dataset.

The single-label training dataset may be created from the image of the multi-label training dataset.

Optionally, a prevalence of the anatomical images labeled with the single visual finding type stored in the single-label training dataset is statistically significantly higher than a prevalence of the anatomical images labeled with the single visual finding type stored in the multi-label training dataset and denoting a wild prevalence of the single visual finding type in practice (e.g., in the population of patients, in the ER, in anatomical images). For example, as described in the experiment section, the multi-label training dataset may include 5828 images depicting pneumothorax, and 2,043, 625 images not depicting pneumothorax, which may be representative of the wild prevalence of pneumothorax in patients undergoing chest x-ray imaging. The prevalence of the images depicting pneumothorax is the single-label training dataset is set to be much higher, for example, about 33% of all images, or about 50%, or about 25-50%, or other values. The higher prevalence may increase the accuracy of the trained single-label neural network in detecting the visual finding type indicative of pneumothorax. The higher prevalence of images depicting pneumothorax may be obtained, for example, by arranging the training images in 3 cyclic queues: "positive", "normal", and "abnormal", optionally each set at ⅓ of the total images, or other distributions may be used. An image is added to the single-label training batch queue by being drawn uniformly at random, and then the next image for training the single-label neural network is obtained from that queue. Hence each batch contains, on average, 33% positive images.

Optionally, the anatomical images of the multi-label training dataset are clustered into three clusters for creating the single-label training dataset having higher prevalence of images depicting the single visual finding type. Exemplary clusters include: a single visual finding type cluster including anatomical images depicting at least the selected single visual finding type (e.g., pneumothorax and another possible finding), a general positive finding cluster including anatomical images depicting at least one of the plurality of visual finding types excluding the selected single visual finding type (e.g. no pneumothorax but one or more other findings), and a negative finding cluster including anatomical images depicting none of the plurality of visual finding types (e.g., no findings). Images may be picked at random from one of the clusters in succession (e.g., from cluster 1, then 2, then 3, then 1 again, and repeated) for insertion into the single-label training dataset, resulting in a pneumothorax prevalence of about 33% in the single-label training dataset.

At 408, a single-label neural network is trained for detection of the single visual finding type in a target anatomical image. It is noted that multiple single-label neural networks may be trained, each one trained independently.

As used herein, the term single-label neural network may refer to the ensemble of instances of the single-label neural network.

The (e.g., each) single-label neural network is trained by setting the trained multi-label neural network as an initial baseline neural network of the single-label neural network. Optionally, with the exception of the last fully-connected layer of the multi-label neural network, the weights from the other corresponding layers of the multi-label neural network were used to initialize the baseline neural network before training.

The baseline neural network may be an architecture adaptation of the multi-label neural network. Different architectures may be used, and/or the same architecture with variation in one or more neural network parameters. The weights of the baseline neural network may be set according to the weights of the trained multi-label neural network. The baseline neural network is fine-tuning and/or re-training according to the single-label training dataset.

An exemplary loss function for training the single-label neural network is a binary cross-entropy loss, mathematically represented as:

$$-z \log(y) - (1-z)\log(1-y)$$

where y denotes the output of the neural network (e.g., between 0 and 1) and z denotes the ground truth (either 0 or 1).

Optionally, the single-label neural network is trained to compute a likelihood score indicative of a probability of the single visual finding type being depicted in the target anatomical image.

Optionally, multiple instances of the single-label neural network are trained using the same baseline and the same single-label training dataset. The instances are created by varying one or more neural network parameters, for example, preprocessing image size, preprocessing input size (i.e., scaling the image to the required input image size), neural network architecture modification, center-crop (e.g., center area of the image, given by the corresponding neural network of the ensemble's input size is extracted out), additional intermediate dense layer(s) before a final output, preprocessing normalization type (e.g., mean of the pre-cropped image is subtracted), and standard deviation normalization (e.g., the standard deviation of the pre-cropped image is divided by). It is noted that the instances of the single-label neural network are different than training different single-label neural networks. All the instances are trained to detect the same visual finding type for the same body region of the same anatomical imaging modality for the same sensor orientation. The different single-label neural networks may differ at least in the detected visual finding type.

Optionally, the performance of each instance is evaluated for detection of the indication of the single visual finding type. A combination of the instances may be selected according to a requirement of the evaluated performance. The combination of instances may be referred to as an ensemble. A set of rules may define how the final indication of likelihood of the visual finding type being present in the target anatomical image is computed from the ensemble, for example, an average of the members of the ensemble, majority vote, and maximum value.

Optionally, the number of selected instances is 2, 3, 4, 5, 6, 7, 8, or greater.

Optionally, each one of the instances computes a score indicative of likelihood of the anatomical image depicting the single visual finding type. The scores are aggregated to compute an aggregated score, for example, by averaging, majority vote, or other methods. When the aggregated score is above a predefined threshold, the image is designated as positive for including the visual finding type. The selection of the threshold may be performed using mini-AUC, as described herein.

At 410, the instances of the single-label neural network included in the ensemble are selected according to a target sensitivity and/or a target specificity. The target sensitivity and/or a target specificity may be provided, for example, manually entered by a user, and/or automatically computed by code. The definition of the target sensitivity and/or a target specificity provides for customization of the performance ability of the single-label neural network, for example, for different hospitals, different radiologists, and/or according to clinical requirements.

Optionally, a mini-AUC (area under curve) is computed for a region under the receiver operating characteristic (ROC) curve computed for each instance of the single-label neural network corresponding to the target sensitivity and/or target specificity. The mini-AUC may be computed as the area under the ROC curve bounded by the target sensitivity, within a tolerance requirement. The tolerance requirement may be provided by the user, automatically defined, and/or provided as a predefined system parameter value. The target sensitivity may denote a lower limit. The specificity may be selected as the maximal specificity within the mini-AUC. One or more instances are selected according to a requirement of the mini-AUC, for inclusion in the ensemble.

Optionally, a sub-region of the ROC defined by the target sensitivity, optionally with a tolerance is computed.

Optionally, the ensemble of instances is selected from a pool of multiple trained neural networks by performing an exhaustive search over all combinations of trained neural networks (e.g., according to a predefined number of neural networks and/or testing combinations with different numbers of neural networks) according to the mini-AUC. The performance of the instances may be computed based on the mini-AUC rather than the full AUC as in traditional methods. The instances with highest performance based on the mini-AUC are selected. For inclusion in the ensemble.

It is noted that the process of computing multiple instances of a neural network, each varying by one or more neural network parameters, and selecting one or more of the trained instances according to a mini-AUC computed for the ROC curve computed for each trained instance corresponding to the target sensitivity and/or target specificity, may be performed for any neural network, and is not necessarily limited to the single-label and multi-label neural networks described herein.

At 412, the trained (optionally selected instances of the) single-label neural network is provided. The provided trained single-label neural network may include an ensemble of instances that differ by combination of neural network parameters. Multiple different trained single-label neural networks may be provided.

EXAMPLES

Reference is now made to the following examples of training the single-label neural network from the multi-label neural network, and analysis of anatomical images by the trained single-label neural network for identification of an indication of a visual finding type denoting an acute medical condition for early and rapid treatment thereof, which together with the above descriptions illustrate some implementations of the systems, methods, apparatus, and/or code instructions described herein in a non limiting fashion.

Inventors performed a computational evaluation according to the systems and/or methods and/or apparatus and/or code instructions described herein, based on the features and/or system components discussed with reference to FIGS. 1-4.

Inventors performed a computational evaluation for training the single-label neural network for detecting an indication of pneumothorax in PA (posterior-anterior) and/or AP (anterior-posterior) two dimensional (2D) chest x-rays.

First, a multi-label neural network was trained. Then, a single-label neural network was trained. The single-label neural network includes an ensemble of four neural network models, denoted A, B, C, and D, which instances of the same single-label neural network, with different adjustments of neural network parameters, as detailed below.

The pre-trained model (i.e., multi-label neural network) was trained from scratch using images from the same training set used to train single-label neural networks A, B, C, and D, and in the same setting, except instead of having a single output (i.e., pneumothorax), it was trained to predict the existence of 57 common x-ray findings (including pneumothorax), using the categorical cross-entropy loss function. With the exception of the last fully-connected layer, the weights from the other layers were used to initialize the other ensemble models before training.

The labels for the 57 common x-ray findings (including pneumothorax) were obtained by a sentence-based analysis of the textual reports of the original 2 million studies, as described herein. When a study has a positive label for a certain finding, the report of that study contained a sentence that was manually reviewed by an expert and found to indicate the presence of the certain finding, as described herein.

Neural networks A, B, C, and D, were fine-tuned from the same pre-trained model based on the multi-label neural network described herein. An ensemble of four neural networks was created, denoted herein as A, B, C, and D. Neural networks A, B, C, and D, were fine-tuned from the same pre-trained model based on the multi-label neural network described herein, where each member of the ensemble differed in one or more neural network parameters. Neural networks A, B, and C have the same setting: (i) Preprocessing image size: 330×330. (ii) Preprocessing input size: 299×299. (iii) Preprocessing normalization: mean normalization AND STD normalization. (iv) Architecture: DenseNet121 as implemented by keras, the output layer has a single unit. Model D has the following setting: (i) Preprocessing image size: 450×450. (ii) Preprocessing input size: 400×400. (iii) Preprocessing normalization: mean normalization. (iv) Architecture: DenseNet121 as implemented by keras, with an additional fully-connected layer of 512 units just before the final output layer (that has a single unit).

Neural Networks A, B, C, and D were trained using the same training set of 5,828 positive (i.e., containing pneumothorax) and 2,043,625 negative (i.e., no pneumothorax) chest x-ray images, with PA and/or AP views. The same training framework was used for all neural networks. In the negative set, 1,446,413 images were "normal" (i.e. no findings at all), and the other 597,212 images were "abnormal" (i.e., at least one abnormal finding other than pneumothorax). During training of each of A, B, C, and D, the training images were arranged in 3 cyclic queues: "positive", "normal", and "abnormal". To add an image to the training batch, a queue was drawn uniformly at random, and then the next image was obtained from that queue. Hence each batch contained, on average, 33% positive images.

The loss function used for training was the binary cross-entropy loss, mathematically represented as:

$$-z \log(y) - (1-z)\log(1-y)$$

Where y denotes the output of the neural network (e.g., between 0 and 1) and z denotes the ground truth (either 0 or 1).

The training was done on a single 1080Ti GPU. The built-in Keras 2.1.3 implementation of DenseNet121 over Tensorflow 1.4 was used. The Adam optimizer with Keras default parameters, and a batch size of 16 was used. An epoch was defined as 150 batches. The starting learning rate was 0.001, which was multiplied by 0.75 when validation loss hadn't improved for 30 epochs. Training was performed for 2000 epochs. The model with the lowest loss on the validation set was selected.

Each x-ray image was preprocessed according to the model specifications, with the following additional augmentations: random horizontal flip, random crop (instead of center-crop), random rotation (up to ±9 degrees), and random zoom (up to ±10%).

The held-out validation set used in the training process (i.e., to select the best model and to determine the threshold) consisted of 532 images (218 positives and 314 negatives). Each image was seen by three expert radiologists. The majority of their opinions (i.e., "No pneumothorax", "There is pneumothorax", "Can't see and can't rule out") was used as the ground-truth (cases without positive or negative majority were removed).

Inventors performed another computational evaluation of an ensemble of single-label neural networks, created based on at least some implementations of the systems, and/or methods described herein.

An engineered validation dataset that includes 532 anatomical images was prepared. The validation dataset that used to quantify the performance of the trained single-label neural networks (i.e. for selection for inclusion in the ensemble) was enriched with cases that are difficult to detect (e.g., difficult for a human to detect and/or difficult for a neural network to detect, for example, small pneumothorax) and/or the prevalence of pneumothorax in the validation dataset was set higher than the prevalence of pneumothorax in anatomical images and/or prevalence in emergency room patients and/or prevalence in the general population. The purpose of the validation dataset was to measure and calibrate the process for detection of pneumothorax by the ensemble on more challenging cases, while giving the challenging cases a higher prevalence than the prevalence measured in the field. The evaluation was also performed to validate that the process for detection of pneumothorax solves successfully also those rare cases.

The validation dataset was engineered to have a diverse cover of a few different subcategories. The validation dataset included 218 positives and 314 negatives, and covered the following subcategories:

Data sources—3, Modality—CR, DX, Manufacturer—5, View—AP, PA, Gender—female, male, Age [y]—18 to 40, 40 to 60, above 60, Co-findings, Size—small, big.

The performance of the selected ensemble in processing the validation dataset was: Sensitivity=90.8%, Specificity=89.5%, and threshold=0.3798732050.

Inventors performed yet another computational evaluation of the ensemble of single-label neural networks, created based on at least some implementations of the systems, and/or methods described herein.

A wild validation dataset that included 1215 images was created. The purpose of the wild validation dataset was to measure the performance of the ensemble of single-label neural networks, created based on at least some implementations of the systems, and/or methods described herein, on negatives that originate from the general population, while giving them a prevalence that resembles the prevalence measured in the field. The evaluation was performed to validate that pneumothorax is successfully solved in the usual cases. The wild validation dataset had the same positives as the validation dataset described above. The wild validation dataset included 218 positives and 997 negatives.

The performance of the selected ensemble in processing the wild validation dataset was: Sensitivity=90.8%, Specificity=95.2%, and threshold=0.3798732.

Furthermore, Inventors discovered that the single-label neural network detects about 80.9% of small pneumothorax in anatomical images. It is noted that small pneumothorax are difficult to detect. One prior art method that attempted to detect pneumothorax with a simple neural network excluded small pneumothorax due to the technical ability to detect them.

Inventors performed an evaluation to compare selection of instances of the single-label neural network (e.g., for inclusion in an ensemble) based on the mini-AUC (as described herein) in comparison to the standard AUC process. Inventors discovered that the mini-AUC is more relevant for selection of instances than the standard AUC process, since the mini-AUC may outperform the standard AUC> For example, for a first instance, the AUC was 95.1% and the mini-AUC (target FPR 85%, tolerance+/−2%) was 93.8%, while for a second instance the AUC was 95.3% and the mini-AUC was 93.6%. The mini-AUC for the first instance was greater than 0.2% than the mini-AUC for the second instance, while the AUC for the first instance was lower than the AUC for the second instance by 0.2%. The actual specificity of the first instance was better by 0.9% at the produced target.

Figure 5:
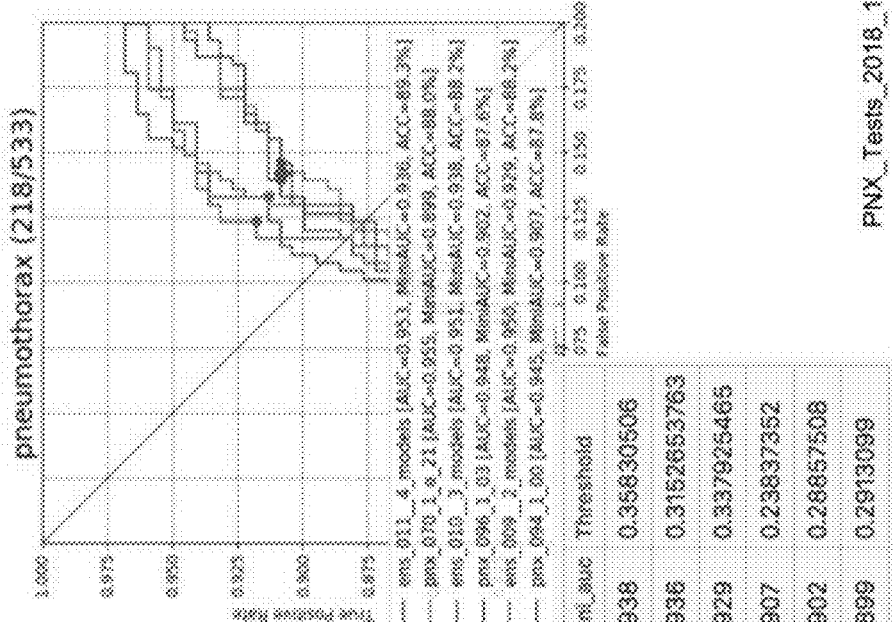
FIG. 5 is a table and graphs summarizing the experimental evaluation for comparison of instances of the single-label neural network based on the mini-AUC in comparison to the standard AUC process, in accordance with some embodiments of the present invention.
Figure 5:
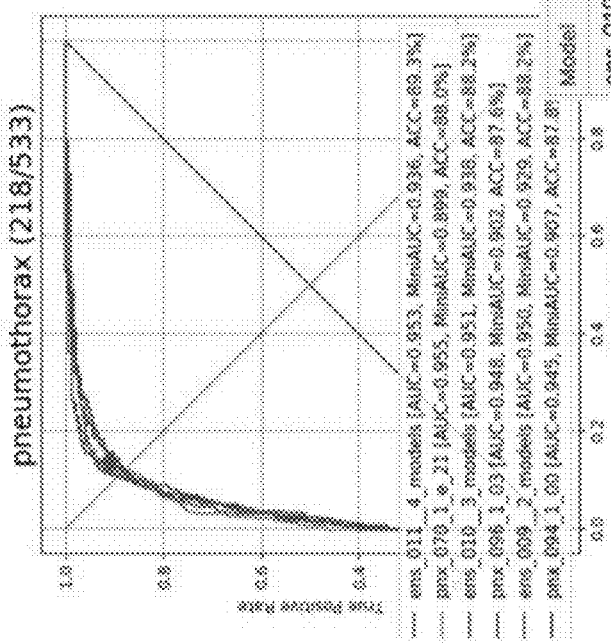

Reference is now made to FIG. 5, which presents a table and graphs summarizing the experimental evaluation for comparison of instances of the single-label neural network based on the mini-AUC in comparison to the standard AUC process, in accordance with some embodiments of the present invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant anatomical images and neural networks will be developed and the scope of the terms anatomical image and neural network are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A system for computing a single-label neural network for detection of an indication of a single visual finding type in an anatomical image of a target individual, the single visual finding type denoting an acute medical condition for early and rapid treatment thereof, comprising:
   at least one hardware processor executing a code for:
      providing a multi-label training dataset including a plurality of anatomical images each associated with a label indicative of at least one visual finding type selected from a plurality of visual findings type, or indicative of no visual finding types;
      training a multi-label neural network for detection of the plurality of visual finding types in a target anatomical image according to the multi-label training dataset;
      creating a single-label training dataset including a plurality of anatomical images each associated with a label indicative of the single visual finding type selected from the plurality of visual finding types used for labelling of the multi-label training dataset, or indicative of an absence of the single visual finding type; and
      training a single-label neural network for detection of the single visual finding type in a target anatomical image, by setting the trained multi-label neural network as an initial baseline of the single-label neural network, and at least one of fine-tuning and re-training the baseline according to the single-label training dataset,
      wherein the single visual finding type detected by the trained single-label neural network is selected from the plurality of visual finding types detected by the trained multi-label neural network.

2. The system of claim 1, wherein the accuracy of the trained single-label neural network for detection of the single visual finding type in the target anatomical image is higher than the accuracy of the multi-label neural network for detection of the single visual finding type in a target anatomical image, and higher than another single-label neural network trained only on the single-label training dataset using a standard un-trained neural network as the initial baseline, and higher than another single-label neural network trained on a multi-object neural network trained to detect non-medical objects in non-medical images.

3. The system of claim 1, wherein detection of the single visual finding type comprises computing, by the single-label neural network, a likelihood score indicative of a probability of the single visual finding type being depicted in the target anatomical image.

4. The system of claim 1, wherein the anatomical image and the single visual finding type are selected from the group consisting of: two dimensional (2D) AP and/or PA and/or lateral chest x-ray and pneumothorax including a small pneumothorax, 2D AP and/or PA chest x-ray and pneumo-mediastinum, and 2D abdominal x-ray and pneumoperitoneum.

5. The system of claim 1, wherein labels of the plurality of anatomical images of the multi-label training dataset are created based on an analysis that maps individual sentences of a plurality of sentences of a respective text based radiology report to a corresponding visual finding type of the plurality of visual finding types.

6. The system of claim 1, wherein the multi-label neural network is trained to identify about 20-50 different visual finding types.

7. The system of claim 1, wherein the plurality of visual finding types include members selected from the group consisting of: abnormal aorta, aortic calcification, artificial valve, atelectasis, bronchial wall thickening, cardiac pacer, cardiomegaly, central line, consolidation, costrophrenic angle blunting, degenerative changes, elevated diaphragm, fracture, granuloma, hernia diaphragm, hilar prominence, hyperinflation, interstitial markings, kyphosis, mass, mediastinal widening, much bowel gas, nodule, orthopedic surgery, osteopenia, pleural effusion, pleural thickening, pneumothorax, pulmonary edema, rib fracture, scoliosis, soft tissue calcification, sternotomy wires, surgical clip noted, thickening of fissure, trachea deviation, transplant, tube, and vertebral height loss.

8. The system of claim 1, wherein training the single-label neural network comprises training a plurality of instances of the single-label neural network, wherein each instance has different neural network parameters, and further comprising:
    evaluating performance of each instance of the plurality of instances for detection of the indication of the single visual finding type; and
    creating an ensemble by selecting a combination of the instances according to a requirement of the evaluated performance,
    wherein single-label neural network comprises the ensemble.

9. The system of claim 8, wherein the different neural network parameters of the plurality of instances of the single-label neural network are selected from the group consisting of: preprocessing image size, preprocessing input size, neural network architecture modification, at least one additional intermediate dense layer before a final output, preprocessing normalization type, and standard deviation normalization.

10. The system of claim 1, wherein training the multi-label neural network comprises training a plurality of instances of the multi-label neural network, and selecting one of the instances having a lowest validation loss for the single visual finding, wherein training the single-label neural network comprises training the selected one instance using a checkpoint of network weights of the selected one instance.

11. The system of claim 1, wherein training the single-label neural network comprises training a plurality of instances of the single-label neural network varying according to at least one network parameter, and further comprising:
    obtaining at least one of a target sensitivity and a target specificity, and a tolerance;
    computing a mini-AUC (area under curve) for a region under the receiver operating characteristic (ROC) curve computed for each instance of the plurality of instances of the single-label neural network, corresponding to the at least one of the target sensitivity and target specificity within the tolerance; and
    selecting at least one instance of the plurality of instances of the single-label neural network according to a requirement of the mini-AUC, for inclusion in an ensemble of the single-label neural network.

12. The system of claim 1, wherein weights of the baseline are set according to corresponding weights of non-last fully connected layers of the trained multi-label neural network.

13. The system of claim 1, wherein a prevalence of the anatomical images labeled with the single visual finding type of the single-label training dataset is statistically significantly higher than a prevalence of the anatomical images labeled with the single visual finding type of the multi-label training dataset and denoting a wild prevalence of the single visual finding type in practice.

14. The system of claim 1, wherein the plurality of anatomical images of the multi-label training dataset are clustered into three clusters, comprising: a single visual finding type cluster including anatomical images depicting at least the single visual finding type, a general positive finding cluster including anatomical images depicting at least one of the plurality of visual finding types excluding the single visual finding type, and a negative finding cluster including anatomical images depicting none of the plurality of visual finding types, wherein the single-label training dataset is created by randomly sampling one image from each of the clusters in succession.

15. A system for detection of an indication of a single visual finding type in a target anatomical image of a target individual by a single-label neural network, the single visual finding type denoting an acute medical condition for early and rapid treatment thereof, comprising:
    at least one hardware processor executing a code for:
        feeding a target anatomical image into a single-label neural network; and
        computing likelihood of an indication of the single visual finding type in the target anatomical image by the single-label neural network,
        wherein the single visual finding type detected by the trained single-label neural network is selected from a plurality of visual finding types detected by a trained multi-label neural network,
        wherein the single-label neural network is computed by at least one of fine-tuning and retraining the trained multi-label neural networking according to a single-label training dataset of a plurality of anatomical images labeled with an indication of the visual finding type selected from the plurality of visual finding types used for labelling of a multi-label training dataset, wherein the multi-label neural network is trained to compute likelihood of each of a plurality of visual finding types based on the multi-label training dataset of a plurality of anatomical images labeled with the plurality of visual finding types.

16. The system of claim 15, further comprising at least one of: diagnosing the acute medical condition and treating the patient for the acute medical condition.

17. The system of claim 15, wherein the feeding, and the computing are iterated for each of a plurality of target anatomical images, and further comprising:
    generating instructions for creating a triage list for manual review by a human user of respective target anatomical images computed as likely including the indication of the visual finding type.

18. The system of claim 17, wherein the visual finding type denotes an acute medical condition requiring urgent treatment, wherein a time delay in diagnosis and treatment of the acute medical condition leads to increased risk of morbidity for the patient.

19. The system of claim 17, wherein the computed likelihood denotes a confidence score indicative of probability of the presence of the visual finding type in the anatomical image, wherein the instructions are for creating the triage list according to priority for review by the human reviewer, ranked by decreasing likelihood of the indication of the visual finding type based on the confidence score.

20. The system of claim 15, further comprising:
    receiving a plurality of target anatomical images from a medical imaging storage server;
    feeding each one of the plurality of target anatomical images into a visual filter neural network for outputting a classification category indicative of a target body region depicted at a target sensor orientation and a rotation relative to a baseline defined by a single-label neural network, or another classification category indicative of at least one of a non-target body region and a non-target sensor orientation;

rejecting a sub-set of the plurality of target anatomical images classified into the another classification category, to obtain a remaining sub-set of the plurality of target anatomical images;

rotating to the baseline the remaining sub-set of the plurality of target anatomical images classified as rotated relative to the baseline; and feeding each one of the remaining sub-set of the plurality of target anatomical images into the single-label neural network for computing likelihood of an indication of the single visual finding type in the respective target anatomical image by the single-label neural network.

21. The system of claim 15, further comprising:

identifying pixels for the target anatomical image having outlier pixel intensity values denoting an injection of content; and adjusting the outlier pixel intensity values of the identified pixels to values computed as a function of non-outlier pixel intensity values, prior to the feeding the target anatomical image into the single-label neural network.

22. A method of computing a single-label neural network for detection of an indication of a single visual finding type in an anatomical image of a target individual, the single visual finding type denoting an acute medical condition for early and rapid treatment thereof, comprising:

providing a multi-label training dataset including a plurality of anatomical images each associated with a label indicative of at least one visual finding type selected from a plurality of visual finding types, or indicative of no visual finding types;

training a multi-label neural network for detection of the plurality of visual finding types in a target anatomical image according to the multi-label training dataset;

creating a single-label training dataset including a plurality of anatomical images each associated with a label indicative of the single visual finding type selected from the plurality of visual finding types used for labelling of the multi-label training dataset, or indicative of an absence of the single visual finding type; and training a single-label neural network for detection of the single visual finding type in a target anatomical image, by setting the trained multi-label neural network as an initial baseline of the single-label neural network, and at least one of fine-tuning and re-training the baseline according to the single-label training dataset, wherein the single visual finding type detected by the trained single-label neural network is selected from the plurality of visual finding types detected by the trained multi-label neural network.

* * * * *